US005687716A

United States Patent [19]
Kaufmann et al.

[11] Patent Number: 5,687,716
[45] Date of Patent: Nov. 18, 1997

[54] SELECTIVE DIFFERENTIATING DIAGNOSTIC PROCESS BASED ON BROAD DATA BASES

[76] Inventors: Peter Kaufmann, Mossvägen 56, Järna, Sweden, 153 37; Håkan Beving, Linnégatan 33-35, Stockholm, Sweden, 114 47; Nils U. Olsson, 6829 Acacia Ct., Frederick, Md. 21703

[21] Appl. No.: 559,032

[22] Filed: Nov. 15, 1995

[51] Int. Cl.$^6$ ................................ A61B 5/00; G06F 3/00
[52] U.S. Cl. ................................ 128/630; 395/23
[58] Field of Search ................ 128/630, 653.1; 364/413.01, 413.02, 413.13; 395/21, 23, 24

[56] References Cited

U.S. PATENT DOCUMENTS

| | | | |
|---|---|---|---|
| 5,331,550 | 7/1994 | Stafford et al. | 364/413.13 |
| 5,463,548 | 10/1995 | Asada et al. | 364/413.02 |
| 5,565,364 | 10/1996 | Schaefer et al. | 436/43 |

OTHER PUBLICATIONS

Wilding, Peter et al, "Appln of . . . Neural Networks to Diagnosis of Breast and Ovarian Cancer," Cancer Letters 77(1994) pp. 145–153.

Mulsont, B.H. "A Neural Networks as an Approach to Clinical Diagnosis," Neural Modelling vol. 7 No. 1 1990 pp. 25–36.

Sharpe, P.K et al "Artificial Neural Networks in Dx of Thyroid Function . . . " Clinical Chemistry vol. 39 No. 1 1993.

Primary Examiner—Francis Jaworski
Attorney, Agent, or Firm—Dorsey & Whitney

[57] ABSTRACT

A process for analyzing for a variety of physical medical disorders, which comprises:

a) clinical testing by a common analysis, patients free of such disorders and those patients that possess such one or more disorders, which analysis distinquishes any such disorder thereby obtaining the characterization of a collection of such disorders as numerical data;

b) scaling the matrix of said numerical data in a computer;

c) configuring in a computer, an artificial neural network prescribed by the number of variables and the number of disorders, which artificial neural network is electronic data that possesses an input layer, one or more hidden layers and an output layer;

d) fitting the artificial neural network electronic data in a computer to the numerical data according to adjustable parameters of the artificial neural network, including one or more of
  i) the number of neurons in a hidden layer;
  ii) the number of hidden layers;
  iii) the type of transfer functions in the layers; and
  iv) the weights connecting the neurons;

e) whereby the artificial neural network is trained in the computer to automatically provide an analytic model;

f) withdrawing from a new patient that has not been diagnosed for such disorder, a sample or samples of a kind taken from said reference patients and subjecting said diagnostic sample to said clinical testing to obtain new numerical data;

g) automatically scaling in the computer the new data to the data derived from the reference patients;

h) feeding the scaled new data to the trained artificial neural network and the analytic model thereof, and i) automatically obtaining a diagnosis of the new patient with respect to such disorders.

13 Claims, No Drawings

SELECTIVE DIFFERENTIATING DIAGNOSTIC PROCESS BASED ON BROAD DATA BASES

BRIEF DESCRIPTION OF THE INVENTION

A diagnostic tool is described that determines a patient's health as to a variety of potential physical and medical disorders. It employs multivariant analysis such as artificial neural networks and partial least squares discriminant analysis in conjunction with standard clinical diagnostic procedures.

BACKGROUND TO THE INVENTION

A physician seeking data about a patient will invariably subject the patient to one or more diagnostic procedures. Blood assays or urine assays, and the like, are ordered and a technician draws blood or procures urine from the patient. These samples are automatically analyzed in an analyzer that can generate considerable amounts of data about the sample, but only the data requested by the physician is fed back to him/her. The quality of the physician's services to the patient depends to a large extent on the data given to the physician and the physician's use of the data. If the data fails to note a symptom of a disorder, then the physician may miss the proper diagnosis. Moreover, physician bias can result in misuse or misunderstanding of data causing diagnosis errors.[1]

[1] Leape, JAMA, volume 272, number 23, pages 1851–1857 (Dec. 21, 1994).

These limitations in the practice of medicine have caused industries to contrive aids that assist the physician in dealing with the data that diagnostic tools are capable of generating. However, such efforts have been limited to specific disorders. Though the tools aid in predicting or finding a disorder with respect to a patient, the tools are so limited that again the data utilized is a mere fraction of that available.

In addition, automatic analyzers are under-utilized because the equipment is not programmed to generate maximum data utilization because of a lack of physician interest in the additional data. Most physicians are incapable of interpreting data other than standard disorder characterizations.

According to Boyd, "Perspectives on the Use of Chemometrics in Laboratory Medicine," Clin. Chem., volume 32, number 9, pages 1726–1733 (1986):

"Measurements and their interpretation are central in the practice of modern medicine. Laboratory medicine as a subspecialty has played an important role in the development of new diagnostic tests and in the generation of an ever-increasing number of measurements. Although modern laboratory instruments produce prodigious amounts of data regarding measurable physiological and chemical qualities, the abundance of these data does not supply specific answers to questions about the physiology or pathophysiology of various organ systems being evaluated. Unless powerful methods can be discovered for converting data to answers, the measurements generated by modern instrumentation may raise more interpretational problems than they solve. In this climate of increasing complexity of data, the necessity for developing tools to aid in interpreting laboratory data has become ever more critical."

A number of systems deal with the data that physiological analysis generates. For example, Drastal et al., *Journal of Medical Systems*, volume 6, number 5, pages 433–445 (1982) describe a so-called EXPERT medical consultation system in which computer models generate rule systems used for diagnosis. Such a system deals with single disorder evaluations and fails to maximally utilize the data generated. In this particular paper, the authors fail to report the success or failure rate for the system.

Another expert approach is described by Kinney et al., *Journal of Medical Systems*, volume 12, number 5, pages 3319–326 (1988). Kinney et al. designate the particular disorder or data collection for evaluation and sort out the evaluation according to a relative scale. Though Kinney et al. have a broader approach to data utilization, it too suffers from the fact that the physician's choice of data viewing limits data utilization.

An interesting approach that uses a multivariant interpretation of the patient's historical data to ascertain evolving abnormalities, is described by H. B. Slotnick et al., *Clinical Chemistry*, volume 36, number 5, pages 748–751 (1990).

Baxt, "Use of an Artificial Neural Network for Data Analysis in Clinical Decision-Making: The Diagnosis of Acute Coronary Occlusion," *Neural Computation*, 2, pages 480–489 (1990) employs an artificial neural network to evaluate the data based on substantial and complex input variables by the physician. As a result, the input is sufficient to allow the physician to diagnose whether the patient has an acute coronary occlusion, drawing into question the need for the use of the artificial neural network, other than to aid in refining the results of the physician's examination.

Snow et al., "Artificial Neural Networks In The Diagnosis And Prognosis Of Prostate Cancer: A Pilot Study," *The Journal Of Urology*, volume 152, pages 1923–1926 (November 1994), describe the analysis for a single disorder, i.e., prostate cancer, based on measurements of serum prostate specific antigen (PSA) and biopsy results of the patient that led to improved false positive and negative conclusions.

Stensmo et al., "A Mixture Model System for Medical and Machine Diagnosis," Teauro, et al. (Ed.) *Advances in Neural Information Processing Systems*, volume 7, Morgan Kaufmann, San Mateo, Calif. (1995) attempt to deal with missing data from an analysis by estimating the parameters of the missing data by the EM algorithm.

There is a need for a method that provides a physician with correct analysis and data, which ascertains a medical disorder characterizable from such data and reports such to the physician without dependence on the foresight of the physician.

There is a need for a method which interprets analytical data in a way that it singles out abnormalities for evaluation which are not obvious from the direct evaluation of data.

In addition to the foregoing needs, the medical profession needs a method that enhances accuracy of diagnosis, especially about conditions considered abnormal to the physician.

Because of the capacity of an automatic analyzer to generate from a patient's sample, data extending beyond that normally selected for determining the existence or non-existence of a disorder, it would be desirable to have a method for using that data for characterizing known or unknown abnormalities.

It is an objective of this invention to satisfy such needs and desires, as well as others, in a facile and effective manner.

THE INVENTION

This invention relates to a process for analyzing for a variety of physical medical disorders, which involves:

1. diagnostically analyzing groups of reference patients using one or more known diagnostic procedures and determining whether the patients possess one or more physical medical disorders;

2. clinical testing by a common analysis, patients free of such disorders and those patients that possess such one or more disorders, which analysis distinquishes any such disorder thereby obtaining the characterization of a collection of numerical data of such one or more disorders;

3. scaling the matrix of said numerical data in a computer;

4. configuring in a computer, an artificial neural network prescribed by the number of variables and the number of disorders, which artificial neural network is electronic data that possesses an input layer, one or more hidden layers and an output layer;

5. fitting the artificial neural network electronic data in a computer to the numerical data according to adjustable parameters of the artificial neural network, including one or more of
   a) the number of neurons in a hidden layer;
   b) the number of hidden layers;
   c) the type of transfer functions in the layers; and
   d) the weights connecting the neurons;

6. whereby the artificial neural network is trained in the computer to automatically provide a analytic model;

7. withdrawing from a new patient that has not been diagnosed for such disorder, a sample or samples of a kind taken from said reference patients and subjecting said diagnostic sample to said clinical testing to obtain new numerical data;

8. automatically scaling in the computer the new numerical data to the numerical data derived from the reference patients;

9. feeding the scaled new numerical data to the trained artificial neural network and the analytic model thereof, and 10. automatically obtaining a diagnostic answer of the new patient with respect to such disorders.

This invention contemplates the use of all forms of clinical, chemical, biochemical and biological diagnoses, e.g., the act or process of identifying or determining the nature and cause of a disease or injury through evaluation of patient history, examination, and review of laboratory data. This includes the diagnostic analysis of bodily fluids, cells, soft and hard tissues, organs, and the like. Such processes include immunoassays, cell size analysis, chromatographic analysis, spectrographic analysis, electrochemical analysis, pH analysis, hematological analysis, ion selective potentiometry and near infrared reflectance spectroscopy (NIR), surface spectroscopy including ion-scattering spectrometry (ISS), secondary ion mass spectrometry (SIMS), and auger emission spectrometry (AES), nuclear magnetic imaging techniques, nuclear magnetic resonance spectrometry (NMR), chemical elemental analysis, gas analysis including gas chromatography, antibody analysis, blotting techniques, electrophoresis, amino acid sequencing, DNA analysis, flow cytometric analysis, ion conductive plasmamass spectrometry (ICP-MS) and atomic absorption spectrometry (AAS), and the like.

Any diagnostic tool applied in the process of the invention is commonly applied in respect to steps (1)–(10) of the process. That means that the assay used in step (1) is applied in step (2) and the results characterized in the remaining steps are based on such assay.

An element of the process is that one intentionally includes in the analysis the diagnoses of healthy patients as well as the diagnoses of afflicted patients. Such provides the basis for comparisons that deal with disorders that are unknown to the patient. For example, a patient complains to the physician of an unspecified illness, which the physician could attribute to a variety of disorder conditions. A sample, such as a blood sample, is taken from the patient and the physician asks for a total comparison with the data from a reference group that is known to possess disorders that exhibit similar symptoms to that of the patient as well as a reference group that has no disorders (i.e., healthy patients). The eventually obtained data that is given to the physician characterizes all deviations from the data of such healthy patients as well as data that correlates with the data of the reference group patients that possess the disorder. However, the results can be presented to the physician in terms of best matching reference group, thereby assigning the particular disorder for the physician. If no matching disorder is found, then the physician in flagged as to any abnormality of the sample. Consequently, the physician can rely on an analysis that is devoid of subjective input coupled with a probability of accuracy. This aids the physician in determining whether to rely on the output of the analysis and allows the physician to couple the analysis with the physician's own diagnosis.

Scaling is the operation of translating data from a variety of different units of measure into a common characterization that one can mathematically employ. Scaling can be done by analog or digital means and the translations can be used by recourse to computation by hand or by computer. However, scaling is best achieved by translating the data on a computer via digital conversions. The preferred method is by autoscaling ("Z transformation") which employs computer programs to automatically digitally translate the data. The scaling removes measurement units. Any distribution, with a certain mean ("$\mu$") and variance ("$\sigma^2$") can be reduced to the same normal or shape distribution with mean 0 and variance 1.

Harrington, *Anal. Chem*, 1994, 66, 802–807, characterizes artificial neural networks as "computational systems that simulate the microstructure of biological nervous systems." He goes on to state:

"These systems have broad application to chemometrics because they are powerful pattern recognizers. Backpropagation neural networks (BNNs) are prevalent in analytical applications. BNNs model relations between sets of input and output data by minimizing errors of the network outputs during training. Information is stored by the strength of the connections between processing layers."

The first step is configuring in a computer, an artificial neural network prescribed by the number of variables and the number of disorders, which artificial neural network is electronic data that possesses an input layer, one or more hidden layers and an output layer. The number of variables gives the number of input neurons and the number of disorders will give the number of output neurons. Determining the number of hidden layers and the number of neurons in the hidden layers is part of the optimization process. Optimization comprises (i) determining the right number of hidden layers, (ii) the right number of neurons in the hidden layers, and (iii) overall training of the network.

Choosing the right numbers of (i) and (ii) above is done by configuring the network by a pre-chosen number (e.g., 1,1 or 1,2) and training this network, calculating the prediction error between the real and the model values, storing this data and choosing the next higher number for the number (i) and (ii) above. In the first step in choosing, the pre-chosen number may be at least one hidden layer and at least two neurons. This new network is trained, and the prediction error calculated and stored. This process is repeated until a minimum prediction error is obtained.

Training of the artificial neural network is a standard procedure in a BNN which evolves by sending data to the network, passing it through the network, receiving the model values and comparing it to the real values, i.e., evaluating the prediction error between the real and model values. This information is back-propagated through the network so that the network weights can be refined stepwise to give selected minimal prediction error. The readjustment is not done haphazardly. All of these steps can be controlled and determined via a computer program.

The selection of type of transfer function in the layer is dependent on the nature of the input data (range of variables), the nature of the output data and the type of answer sought. For a hidden layer one may use the hyperbolic tangent sigmoid function, and for the output neuron, a logistic sigmoid function. However, other functions exist and may be employed instead. For example, a linear transfer function, a threshold function, binary hard limiter, bipolar hard limiter, and the like functions, can be employed instead.

The artificial neural network model can be employed in similarly treating the diagnoses of a sample or samples withdrawn from a new patient that has not been diagnosed for such disorder. The same scaling factors can be used so that the computer automatically calculates the diagnoses.

DETAILED DESCRIPTION OF THE INVENTION

This invention relates to the use of computer analyses using computing and analytical programs located on a computer hard drive (or optical, magnetic and other memory units), plug-in board, expansion box of a computer containing a standard 486/Pentium or Apple Mac microprocessor (or a later generation microprocessor), employing a standard monitor screen. The invention can be practiced on micro, mini and large frame computers using any basic or specialized operating system such as DOS, UNIX, Windows 3.1, 3.11 and Window95, Windows NT, MAC, Apple, and the like, operating systems. The invention can also be placed on the analytical instrument proper utilizing internal computing resources.

The first step in the process of the invention involves determining the analytical parameters to which the patients will be subjected. For example, the analyses can relate to any physiological, chemical and/or pathological issue, without limitation. The analyses can relate to any aspect or all aspects of blood analyses that determine heart related issues, infectious disease disorders, circulatory disease disorders, neural disorders, genetically related issues such as inborn errors of metabolism, disorders related to environmental issues, and the like. The analyses can be of cells, all manner of hard and soft tissues, urine, feces, semen and tissue biopsies, and the like. The analyses (e.g. of blood gases) can relate to all manner of physiological gas and fluid constituents. Having said all of that, it is obvious that the extension of the invention to such a variety of analyses will result in an abundance of data that transcends that requested or designated by the physician seeking the analyses.

The first step is the collection of the reference groups used in the analyses. This done by 1. subjecting a candidate reference patient to examination to determine whether or not the patient suffers from the disorder under investigation and categorization.
2. collecting the data from as many patients as possible with the disorder. Because such candidate reference patient is regarded to be abnormal because the patient possesses the disorder, a broad spectrum of data is procured about that patient for use in assessing trends in the reference patients and the new patients.

For example, the following table is a calibration set of blood analysis data from a number of reference patients and healthy controls for the purpose of testing the blood of reference patients with diagnosed heart disease, each of whom was schedule for bypass surgery, reference patients suffering from dental amalgam syndrome, reference patients suffering from exposure to organic solvents, acrylic latex paints, and finally, a control group of healthy patients:

Calibration set:

TABLE 1

| Patient code | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| A1A3 | 6.3 | 4.32 | 12.6 | 40.1 | 92.9 | 29.1 | 31.3 | 136 | 30.8 | 1.9 | 11.7 | 9.4 | 0.09 | 6.8 | 8.8 | 9 | 4.4 | 89 | 147 |
| A1B3 | 9.4 | 5.4 | 15.4 | 46.2 | 89.2 | 28.6 | 32.1 | 186 | 17.1 | 1.6 | 12.3 | 9.4 | 0.12 | 6.6 | 8.7 | 8.9 | 4.6 | 85 | 152 |
| A1G3 | 6.1 | 4.88 | 14.8 | 50.3 | 103.2 | 30.4 | 29.4 | 155 | 40.1 | 2.5 | 10.1 | 10.1 | 0.11 | 7.1 | 8.2 | 8.5 | 5.4 | 92 | 144 |
| A2A3 | 6.4 | 5.32 | 15.6 | 43.9 | 82.6 | 29.4 | 35.6 | 206 | 28.4 | 1.8 | 10.6 | 8.1 | 0.14 | 7 | 8.6 | 8.8 | 4.7 | 91 | 137 |
| A2D3 | 8.8 | 5.95 | 17.5 | 49.6 | 83.4 | 29.4 | 35.2 | 195 | 20.7 | 1.8 | 10.8 | 8.1 | 0.13 | 6.9 | 8.3 | 8.6 | 5 | 93 | 145 |
| A2E3 | 4.8 | 5.55 | 15.1 | 43 | 77.6 | 27.3 | 35.1 | 135 | 26.1 | 1.3 | 11 | 8.2 | 0.09 | 6.6 | 8.3 | 8.7 | 5 | 85 | 141 |
| A2G3 | 6.8 | 5.5 | 15.4 | 43.6 | 79.2 | 28.1 | 35.5 | 208 | 38.7 | 2.6 | 10.9 | 8.1 | 0.14 | 6.8 | 8.5 | 8.7 | 4.6 | 88 | 138 |
| A2H3 | 6.9 | 5.88 | 16.2 | 47 | 80 | 27.6 | 34.5 | 228 | 24.4 | 1.7 | 11.4 | 8.3 | 0.16 | 7 | 8.4 | 8.7 | 4.9 | 87 | 133 |
| A2J3 | 14.9 | 5.99 | 16.5 | 47.2 | 78.8 | 27.5 | 34.9 | 194 | 19.9 | 3 | 10.9 | 8.2 | 0.126 | 6.5 | 8.5 | 8.7 | 5.2 | 87 | 144 |
| A2K3 | 6.3 | 5.27 | 16.1 | 44.7 | 84.8 | 30.6 | 36.1 | 128 | 31.9 | 2 | 10.9 | 8.2 | 0.08 | 6.2 | 8.3 | 8.7 | 4.4 | 93 | 139 |
| A2L3 | 6.5 | 5.4 | 16.4 | 45.8 | 84.9 | 30.4 | 35.8 | 147 | 41.8 | 2.7 | 10.1 | 8.1 | 0.104 | 7 | 8.6 | 8.7 | 5.5 | 95 | 141 |
| A3B3 | 5.5 | 5.78 | 15.8 | 45.9 | 76.5 | 27.5 | 35.9 | 156 | 26.1 | 1.5 | 10.6 | 8.1 | 0.112 | 7.2 | 8.6 | 8.9 | 5.2 | 85 | 145 |
| A3D3 | 9.8 | 5.31 | 15 | 44.1 | 83.2 | 28.3 | 34 | 186 | 31 | 3 | 11 | 8.1 | 0.128 | 6.9 | 8.3 | 8.6 | 5.8 | 93 | 149 |
| A3E3 | 7.9 | 5.3 | 14.8 | 42.8 | 80.7 | 27.9 | 34.7 | 226 | 46.3 | 3.6 | 10.5 | 8 | 0.147 | 6.5 | 8.3 | 8.6 | 4.8 | 91 | 152 |
| A3F3 | 6.1 | 5.48 | 16.4 | 45.7 | 83.4 | 29.7 | 35.7 | 160 | 23 | 1.3 | 11.2 | 8.2 | 0.105 | 6.6 | 8.5 | 8.7 | 4.2 | 92 | 143 |
| A3G3 | 10.6 | 5.07 | 14.5 | 39.2 | 77.4 | 28.5 | 36.8 | 268 | 26.4 | 2.9 | 11.6 | 8.2 | 0.181 | 6.7 | 8.2 | 8.6 | 4.7 | 85 | 142 |
| A3H3 | 6.2 | 6.35 | 18.1 | 51.8 | 81.6 | 28.5 | 35 | 176 | 30.2 | 1.9 | 11.3 | 8.1 | 0.128 | 7.3 | 8.4 | 8.7 | 5.6 | 91 | 154 |
| A3I3 | 8.9 | 4.72 | 14.2 | 39.9 | 84.6 | 30.1 | 35.6 | 413 | 16.8 | 1.5 | 11.8 | 8.1 | 0.269 | 6.5 | 8.5 | 8.8 | 4.1 | 95 | 167 |
| A3M3 | 6.4 | 5.58 | 16.1 | 45.4 | 81.4 | 28.8 | 35.4 | 214 | 35.9 | 2.3 | 10.9 | 8.1 | 0.152 | 7.1 | 8.5 | 8.8 | 5.4 | 90 | 145 |
| Amlgm1 | 12.5 | 4.35 | 17.4 | 45.1 | 103.7 | 40.1 | 38.7 | 193 | 22.5 | 2.8 | 11.1 | 9.2 | 0.13 | 6.6 | 8.6 | 8.8 | 5.3 | 102 | 176 |
| Amlgm2 | 5.9 | 4.2 | 13.4 | 39.7 | 94.4 | 31.9 | 33.8 | 135 | 38 | 2.3 | 10.8 | 9.3 | 0.1 | 7.7 | 9 | 9.2 | 5.8 | 92 | 154 |
| Amlgm3 | 8 | 4.24 | 13.7 | 40.6 | 95.6 | 32.2 | 33.7 | 150 | 33 | 2.6 | 10.8 | 9.1 | 0.12 | 7.7 | 8.7 | 8.9 | 6.5 | 96 | 158 |
| Amlgm4 | 6.7 | 5.07 | 19.1 | 46.5 | 96.6 | 37.7 | 41.2 | 191 | 37.1 | 2.5 | 10.7 | 9.2 | 0.12 | 6.5 | 8.6 | 8.8 | 5 | 90 | 174 |
| Amlgm6 | 6 | 4.25 | 14.4 | 39.6 | 93.2 | 34 | 36.4 | 112 | 35.1 | 2.1 | 9.8 | 9.2 | 0.08 | 7.4 | 9 | 9.2 | 6.2 | 92 | 170 |
| Amlgm7 | 7 | 4.55 | 15.5 | 41.9 | 92.1 | 34.1 | 37 | 149 | 26.8 | 1.9 | 9.8 | 9.1 | 0.11 | 7.6 | 8.7 | 8.8 | 6.2 | 92 | 176 |
| Amlgm8 | 14.2 | 4.81 | 17 | 45.6 | 94.9 | 35.4 | 37.4 | 169 | 21.5 | 3.1 | 10.5 | 9.4 | 0.12 | 7 | 8.6 | 8.8 | 5.8 | 92 | 172 |
| Amlgm9 | 8.3 | 4.35 | 15.3 | 41.7 | 95.7 | 35.1 | 36.6 | 159 | 38.6 | 3.2 | 10.6 | 9.4 | 0.11 | 7.2 | 8.4 | 8.6 | 5.6 | 92 | 166 |

TABLE 1-continued

| Patient code | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| Amlgm10 | 8.2 | 5.44 | 18 | 49.3 | 90.7 | 33.1 | 36.5 | 147 | 33.3 | 2.7 | 11.1 | 9.3 | 0.11 | 7.2 | 8.6 | 8.8 | 6.4 | 88 | 168 |
| Amlgm11 | 10.6 | 4.58 | 16.3 | 44 | 96.1 | 35.7 | 37.2 | 166 | 33.3 | 3.5 | 10.1 | 9.2 | 0.12 | 7.1 | 8.5 | 8.8 | 6.2 | 94 | 162 |
| Amlgm13 | 6.2 | 4.38 | 14.3 | 39.1 | 89.3 | 32.6 | 36.5 | 169 | 41.1 | 2.5 | 11.8 | 9.4 | 0.13 | 7.4 | 8.6 | 8.8 | 6.2 | 86 | 160 |
| Amlgm14 | 6.1 | 4.86 | 17.1 | 46.2 | 95.3 | 35.2 | 36.9 | 146 | 40.9 | 2.5 | 10.3 | 9.2 | 0.11 | 7.2 | 8.8 | 9 | 5.2 | 92 | 166 |
| Amlgm15 | 8.8 | 4.85 | 17.3 | 48.8 | 100.5 | 35.7 | 35.5 | 170 | 28.4 | 2.5 | 10.7 | 9.2 | 0.11 | 6.7 | 8.5 | 8.8 | 5.2 | 98 | 166 |
| Amlgm16 | 5.8 | 3.87 | 13.3 | 37.7 | 97.2 | 34.4 | 35.4 | 158 | 36.4 | 2.1 | 9.8 | 9.1 | 0.11 | 7.1 | 8.9 | 9.1 | 6.4 | 96 | 162 |
| Amlgm17 | 5.6 | 5.21 | 16.5 | 48.8 | 93.8 | 31.8 | 33.9 | 221 | 25.6 | 1.4 | 11.2 | 9.3 | 0.15 | 6.8 | 8.9 | 9.1 | 4.6 | 90 | 160 |
| Amlgm20 | 5.6 | 4.89 | 15.7 | 44 | 89.9 | 32.1 | 35.7 | 163 | 32.4 | 1.9 | 10.6 | 9.2 | 0.12 | 7.2 | 8.4 | 8.7 | 6.4 | 88 | 160 |
| Amlgm23 | 5.1 | 4.15 | 11.7 | 38.4 | 92.6 | 28.1 | 30.4 | 201 | 35.5 | 1.8 | 10.8 | 9.2 | 0.14 | 7.2 | 8.4 | 8.7 | 5.4 | 90 | 152 |
| Amlgm24 | 7.2 | 5.13 | 13.2 | 43.8 | 85.5 | 25.6 | 30 | 240 | 20.1 | 1.4 | 11.9 | 9.3 | 0.17 | 7.1 | 8.5 | 8.7 | 5.8 | 84 | 154 |
| Amlgm25 | 6.8 | 4.41 | 12 | 38.6 | 87.6 | 27.2 | 31 | 233 | 28.6 | 1.9 | 10.8 | 9.2 | 0.17 | 7.2 | 7.9 | 8.3 | 6 | 86 | 150 |
| OrgSolv73 | 4.7 | 4.45 | 16.6 | 42.4 | 95.3 | 37.3 | 39.2 | 226 | 31.5 | 1.5 | 9.9 | 8.6 | 0.141 | 6.2 | 10.1 | 10 | 4.5 | 99 | 172 |
| OrgSolv74 | 4.8 | 4.55 | 15.5 | 40.4 | 88.8 | 34 | 38.3 | 200 | 40.7 | 2 | 10.3 | 8.7 | 0.13 | 6.5 | 9.8 | 9.8 | 5 | 92 | 113 |
| OrgSolv98 | 4 | 5.1 | 16.6 | 49.7 | 96.7 | 32.4 | 33.5 | 226 | 27 | 1.1 | 10.6 | 9.6 | 0.158 | 7 | 9.8 | 9.8 | 5.9 | 91 | 153 |
| OrgSolv99 | 9.7 | 5.2 | 16.4 | 49.1 | 94.1 | 31.3 | 33.3 | 460 | 29 | 2.8 | 10.5 | 9.6 | 0.328 | 7.1 | 9.2 | 9.3 | 5.2 | 88 | 151 |
| OrgSolv67 | 4.5 | 4.23 | 14.9 | 38.1 | 90.2 | 35.2 | 39 | 169 | 50.8 | 2.3 | 10.3 | 8.7 | 0.104 | 6.2 | 9.7 | 9.6 | 4.8 | 93 | 93 |
| OrgSolv68 | 4.1 | 4.86 | 15.9 | 41.7 | 85.9 | 32.8 | 38.2 | 178 | 34 | 1.4 | 10.7 | 10.3 | 0.125 | 7.1 | 10.4 | 10.3 | 6.2 | 89 | 161 |
| OrgSolv84 | 4.1 | 5.4 | 16.5 | 51.2 | 94.5 | 30.4 | 32.2 | 260 | 35.1 | 1.5 | 10.8 | 9.5 | 0.166 | 6.4 | 9.2 | 9.3 | 5.1 | 89 | 149 |
| OrgSolv85 | 7.2 | 4.8 | 16.6 | 48.8 | 100.7 | 34.2 | 34 | 329 | 29.1 | 2.1 | 10.8 | 9.6 | 0.191 | 5.8 | 9.1 | 9.3 | 4.6 | 95 | 163 |
| OrgSolv94 | 4.2 | 4.6 | 15.7 | 45 | 98.5 | 34.2 | 34.7 | 222 | 25.2 | 1.1 | 9.8 | 9.6 | 0.148 | 6.7 | 9.1 | 9.2 | 5.7 | 92 | 152 |
| OrgSolv95 | 3.8 | 5.2 | 17.2 | 51 | 97.9 | 33 | 33.7 | 289 | 23.2 | 0.9 | 10.9 | 9.7 | 0.188 | 6.5 | 9.1 | 9.2 | 5 | 91 | 155 |
| OrgSolv96 | 5.8 | 5 | 15.7 | 47.5 | 95.7 | 31.4 | 32.9 | 276 | 38.3 | 2.2 | 10.4 | 9.5 | 0.183 | 6.6 | 9.2 | 9.2 | 5.1 | 91 | 137 |
| OrgSolv70 | 5.9 | 4.74 | 16.8 | 43 | 90.7 | 35.3 | 38.9 | 218 | 32.3 | 1.9 | 10.6 | 8.7 | 0.15 | 6.9 | 10.6 | 10.4 | 5.5 | 94 | 171 |
| OrgSolv71 | 4.1 | 4.54 | 16 | 43 | 94.8 | 35.3 | 37.2 | 157 | 25.6 | 1 | 9.3 | 8.6 | 0.104 | 6.6 | 10 | 9.9 | 5 | 100 | 166 |
| OrgSolv72 | 4.8 | 4.8 | 16.4 | 43.4 | 90.4 | 34.2 | 37.9 | 204 | 49.3 | 2.4 | 9.8 | 8.5 | 0.118 | 5.9 | 9.3 | 9.4 | 4.5 | 95 | 91 |
| OrgSolv64 | 6.2 | 4.15 | 13.1 | 37.7 | 91 | 31.6 | 34.7 | 272 | 37.6 | 2.3 | 10.6 | 8.6 | 0.194 | 7.1 | 10.4 | 10.3 | 6.2 | 95 | 153 |
| OrgSolv65 | 3.8 | 4.58 | 15.1 | 42.3 | 92.3 | 33.1 | 35.8 | 232 | 35.7 | 1.3 | 10.3 | 8.7 | 0.138 | 5.9 | 10.8 | 10.7 | 2.9 | 95 | 127 |
| OrgSolv66 | 4.7 | 4.4 | 15.3 | 40.2 | 91.4 | 34.8 | 38 | 211 | 45.3 | 2.1 | 9.8 | 8.6 | 0.146 | 6.9 | 9.7 | 9.7 | 5 | 95 | 95 |
| OrgSolv91 | 3.7 | 5.1 | 16.8 | 49.2 | 96.1 | 32.7 | 34.1 | 223 | 32.9 | 1.2 | 10.8 | 9.8 | 0.147 | 6.6 | 9.5 | 9.5 | 5 | 88 | 145 |
| OrgSolv92 | 7.8 | 5.1 | 16.6 | 49.5 | 97.4 | 32.7 | 33.6 | 353 | 24.2 | 1.9 | 10.7 | 9.5 | 0.223 | 6.3 | 8.7 | 8.9 | 5.1 | 93 | 149 |
| OrgSolv93 | 4.7 | 5.2 | 16.9 | 49.4 | 94.5 | 32.2 | 34.2 | 151 | 24.2 | 1.2 | 10.7 | 9.7 | 0.106 | 7 | 10.5 | 10.4 | 4.5 | 88 | 149 |
| OrgSolv88 | 3.6 | 4.8 | 16.8 | 50 | 103.6 | 34.9 | 33.7 | 222 | 44.7 | 1.6 | 10.3 | 9.5 | 0.158 | 7.1 | 9.7 | 9.7 | 5.7 | 98 | 111 |
| OrgSolv88 | 4.9 | 4.3 | 14.9 | 44.9 | 103.4 | 34.3 | 33.1 | 256 | 42.6 | 2.1 | 9.8 | 9.4 | 0.186 | 7.3 | 9.2 | 9.2 | 6.7 | 99 | 87 |
| OrgSolv90 | 4.9 | 5 | 16.6 | 48.8 | 96.9 | 33.1 | 34.1 | 334 | 36.8 | 1.8 | 10.1 | 9.5 | 0.213 | 6.4 | 8.8 | 9 | 5.1 | 92 | 132 |
| OrgSolv61 | 6.2 | 4.88 | 15.9 | 43.3 | 88.7 | 32.7 | 36.8 | 230 | 32.6 | 2 | 10.5 | 8.9 | 0.148 | 6.4 | 10.1 | 10 | 4.3 | 90 | 149 |
| OrgSolv62 | 3.9 | 4.5 | 14.6 | 40.9 | 91.1 | 32.5 | 35.6 | 238 | 41.7 | 1.7 | 10.1 | 8.8 | 0.155 | 6.5 | 10.2 | 10.1 | 5.2 | 93 | 113 |
| OrgSolv63 | 4 | 4.48 | 14.8 | 41.4 | 92.4 | 32.9 | 35.6 | 230 | 28.6 | 1.1 | 10.1 | 8.6 | 0.154 | 6.7 | 10.1 | 10 | 6 | 97 | 143 |
| Orgsolv76 | 5.5 | 4.79 | 16.1 | 42.8 | 89.2 | 33.5 | 37.6 | 114 | 28 | 1.5 | 10.3 | 8.7 | 0.087 | 7.6 | 10.5 | 11 | 2.7 | 92 | 162 |
| OrgSolv77 | 6.3 | 4.83 | 16.8 | 43.3 | 89.3 | 34.6 | 38.7 | 241 | 32.4 | 2 | 10 | 8.7 | 0.152 | 6.3 | 9.1 | 9.2 | 5.3 | 93 | 173 |
| OrgSolv78 | 4.8 | 4.65 | 16 | 41.7 | 89 | 34.5 | 38.7 | 220 | 50.9 | 2.4 | 9.7 | 8.6 | 0.137 | 6.2 | 9.3 | 9.4 | 5 | 93 | 91 |
| OrgSolv60 | 3.6 | 5.28 | 16 | 43.6 | 82.4 | 30.3 | 36.8 | 204 | 34.8 | 1.2 | 11 | 8.9 | 0.129 | 6.4 | 10 | 10 | 5.2 | 83 | 158 |
| OrgSolv79 | 3.5 | 4.7 | 15.7 | 41.7 | 88.7 | 33.4 | 37.6 | 110 | 40.6 | 1.4 | 10.2 | 8.6 | 0.075 | 6.8 | 10.5 | 10.3 | 5.4 | 93 | 133 |
| OrgSolv80 | 4.3 | 4.34 | 15.1 | 39 | 89.8 | 34.8 | 38.8 | 133 | 46.8 | 2 | 10.4 | 8.8 | 0.098 | 7.3 | 10.5 | 10.4 | 6.5 | 92 | 89 |
| OrgSolv81 | 5.7 | 4.7 | 15 | 44.4 | 94.1 | 31.8 | 33.8 | 226 | 37.9 | 2.1 | 10.1 | 9.6 | 0.161 | 7.1 | 9.4 | 9.4 | 5.3 | 88 | 145 |
| OrgSolv82 | 7.2 | 4.9 | 17.1 | 46.8 | 94.7 | 34.5 | 36.5 | 461 | 30.9 | 2.2 | 10.4 | 9.7 | 0.26 | 5.6 | 8.2 | 8.5 | 4.6 | 88 | 153 |
| OrgSolv86 | 5.4 | 4.6 | 14.9 | 45.3 | 98 | 32.3 | 33 | 339 | 39.2 | 2.1 | 10.1 | 9.5 | 0.226 | 6.7 | 9.1 | 9.2 | 5.2 | 93 | 155 |
| Acryl10 | 6.7 | 4.97 | 14.7 | 44 | 88.5 | 29.7 | 33.5 | 242 | 31.9 | 2.1 | 10.2 | 9.1 | 0.164 | 6.7 | 10.8 | 10.6 | 3.7 | 89 | 127 |
| Acryl12 | 7.5 | 4.72 | 15.3 | 45.4 | 96.1 | 32.4 | 33.7 | 307 | 18.5 | 1.4 | 9 | 9 | 0.173 | 5.6 | 10.1 | 10 | 3.1 | 96 | 138 |
| Acryl13 | 5 | 4.28 | 14.7 | 44.2 | 103.2 | 34.3 | 33.2 | 217 | 39.1 | 2 | 9.2 | 8.9 | 0.144 | 6.6 | 9.7 | 8.9 | 5.2 | 105 | 92 |
| Acryl1 | 4.8 | 4.85 | 14.5 | 43.8 | 90.4 | 30 | 33.2 | 328 | 40 | 1.9 | 9.6 | 9.1 | 0.184 | 5.6 | 10 | 10 | 3 | 88 | 88 |
| Acryl2 | 6.3 | 6.92 | 14.4 | 42.8 | 87 | 29.2 | 33.6 | 339 | 21.3 | 1.3 | 9.6 | 9 | 0.185 | 5.5 | 10.2 | 10.1 | 3 | 88 | 132 |
| Acryl22 | 5.3 | 5 | 15.5 | 46.1 | 90.5 | 30.5 | 33.6 | 347 | 36.6 | 1.9 | 10 | 9.2 | 0.2 | 5.8 | 9.5 | 9.5 | 3.9 | 89 | 105 |
| Acryl24 | 5.5 | 4.1 | 13.4 | 40.4 | 98.4 | 32.8 | 33.3 | 192 | 25.7 | 1.4 | 9.7 | 9.1 | 0.132 | 6.8 | 9.3 | 9.4 | 5.6 | 98 | 146 |
| Acryl25 | 7.6 | 4.93 | 15 | 45 | 91.3 | 30.5 | 33.4 | 338 | 32.8 | 2.5 | 9.2 | 9.1 | 0.193 | 5.7 | 10 | 9.9 | 4.3 | 91 | 154 |
| Acryl26 | 4.2 | 3.9 | 12.9 | 39.4 | 101 | 33.1 | 32.8 | 272 | 32.4 | 1.4 | 9.2 | 9.1 | 0.185 | 6.8 | 10.4 | 10.3 | 4.8 | 100 | 163 |
| Acryl4 | 5.2 | 4.72 | 14.3 | 41.6 | 89.6 | 30.3 | 33.8 | 308 | 27.5 | 1.4 | 9.5 | 9 | 0.164 | 5.7 | 10 | 9.9 | 3.1 | 89 | 135 |
| Acryl5 | 4.1 | 4.18 | 13.5 | 40.6 | 97 | 32.2 | 33.3 | 210 | 40.5 | 1.7 | 9 | 9.6 | 0.131 | 6.2 | 10.6 | 9.6 | 4.7 | 98 | 83 |
| Acryl6 | 7.6 | 4.96 | 14.8 | 45.1 | 91 | 29.8 | 32.8 | 312 | 30 | 2.2 | 8.9 | 8.9 | 0.181 | 5.8 | 10.4 | 10.3 | 3.6 | 92 | 150 |
| Acryl42 | 5.1 | 4.36 | 13.4 | 40.3 | 92.5 | 30.8 | 33.1 | 318 | 30.8 | 1.5 | 9.1 | 9 | 0.196 | 6.1 | 11 | 10.8 | 3 | 92 | 109 |
| Acryl8 | 5.4 | 4.2 | 13.1 | 39 | 92.8 | 31.3 | 33.6 | 324 | 27.2 | 1.5 | 9.4 | 9.1 | 0.19 | 5.8 | 9.8 | 9.7 | 4 | 92 | 150 |
| Acryl9 | 6.5 | 4.86 | 15.4 | 43.8 | 90 | 30.3 | 33.8 | 255 | 24.6 | 1.6 | 10 | 9.2 | 0.201 | 6.7 | 10.5 | 10.3 | 4.6 | 93 | 148 |
| Acryl14 | 4.9 | 5.25 | 15.6 | 46.6 | 88.8 | 29.7 | 33.4 | 248 | 31.3 | 1.5 | 9.8 | 9.3 | 0.157 | 6.3 | 10.9 | 10.7 | 3.2 | 88 | 134 |
| Acryl16 | 7.2 | 4.94 | 16 | 45.5 | 92.2 | 32.3 | 35.1 | 294 | 44.5 | 3.2 | 10.3 | 8.7 | 0.169 | 6.9 | 10.7 | 10.5 | 4.6 | 95 | 94 |
| Acryl17 | 9.6 | 5.19 | 15.3 | 46.4 | 89.3 | 29.6 | 33.1 | 342 | 22.4 | 2.2 | 9.4 | 9.1 | 0.226 | 6.6 | 10.3 | 10.2 | 3.9 | 89 | 146 |
| Acryl30 | 5.6 | 4.17 | 13 | 40 | 96 | 31.2 | 32.5 | 242 | 31 | 1.7 | 9.2 | 9.1 | 0.173 | 7.1 | 10.8 | 10.6 | 4.4 | 96 | 147 |
| Acryl31 | 6 | 4.79 | 14.1 | 43.3 | 90.4 | 29.5 | 32.6 | 207 | 35.5 | 2.2 | 8.8 | 9.1 | 0.133 | 6.4 | 10.2 | 10.1 | 4.2 | 90 | 108 |
| Acryl33 | 5.4 | 4.67 | 14.4 | 43.2 | 92.5 | 30.9 | 33.4 | 274 | 30.4 | 1.6 | 9.1 | 9.1 | 0.173 | 6.2 | 10 | 9.9 | 4.6 | 92 | 140 |
| Acryl38 | 4.6 | 4.86 | 14.3 | 43.1 | 88.5 | 29.6 | 33.4 | 246 | 44.3 | 2 | 9.5 | 9.1 | 0.155 | 6.2 | 11.2 | 11 | 3 | 88 | 86 |
| Acryl39 | 8.8 | 5.61 | 16.4 | 48.9 | 87.2 | 29.2 | 33.5 | 226 | 33.7 | 2.9 | 9.7 | 9 | 0.163 | 7.3 | 10 | 11.9 | 3.5 | 87 | 87 |
| Acryl18 | 6.2 | 4.68 | 14.9 | 44.7 | 95.6 | 31.7 | 33.2 | 283 | 25.1 | 1.5 | 9 | 9 | 0.178 | 6.3 | 10 | 10 | 4.1 | 96 | 141 |
| Acryl19 | 5.7 | 4.31 | 13.4 | 39.2 | 92.3 | 31.1 | 33.7 | 269 | 20.1 | 1.1 | 8.8 | 9.5 | 0.171 | 6.3 | 10.9 | 10.7 | 3.1 | 92 | 139 |
| Acryl20 | 5.6 | 4.67 | 14.3 | 43.3 | 92.8 | 30.6 | 32.9 | 293 | 27.5 | 1.6 | 9 | 9 | 0.124 | 6.3 | 10.5 | 10.3 | 3 | 93 | 140 |
| aC1 | 5.5 | 4.53 | 11.5 | 37.8 | 83.6 | 25.4 | 30.4 | 180 | 35.7 | 2 | 11.5 | 9.3 | 0.12 | 6.8 | 8.1 | 8.5 | 5.4 | 82 | 144 |
| aC2 | 5.9 | 4.38 | 12.5 | 40.7 | 92.9 | 28.5 | 30.7 | 175 | 29.9 | 1.7 | 10.6 | 9.1 | 0.12 | 6.7 | 8.2 | 8.6 | 5 | 92 | 152 |
| aC3 | 3.9 | 4.59 | 12.8 | 41.4 | 90.2 | 27.9 | 30.9 | 153 | 41.7 | 1.6 | 10.4 | 9.1 | 0.1 | 6.5 | 8 | 8.4 | 5.2 | 90 | 150 |
| aC4 | 6.1 | 5.04 | 14.4 | 46 | 91.3 | 28.6 | 31.3 | 175 | 30.7 | 1.9 | 10.9 | 9.1 | 0.11 | 6.4 | 8.1 | 8.4 | 4.6 | 90 | 150 |

TABLE 1-continued

| Patient code | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| aC5 | 6.3 | 4.94 | 14.1 | 44.9 | 90.8 | 28.5 | 31.4 | 178 | 39.7 | 2.5 | 11.1 | 9.3 | 0.13 | 7.5 | 8.5 | 8.8 | 5.8 | 88 | 154 |
| aC7 | 2.9 | 4.74 | 12.3 | 40.7 | 85.6 | 26 | 30.3 | 108 | 45.9 | 1.3 | 11 | 9.2 | 0.08 | 7.4 | 8.3 | 8.6 | 5.8 | 84 | 154 |
| aC8 | 5.2 | 5.27 | 14.4 | 45.7 | 86.8 | 27.3 | 31.9 | 143 | 34 | 1.8 | 11.6 | 9.2 | 0.11 | 7.5 | 8.5 | 8.8 | 5.8 | 84 | 148 |
| C13 | 4.3 | 5.09 | 16.7 | 43.2 | 84.9 | 32.8 | 38.7 | 147 | 34 | 1.4 | 11.9 | 9.4 | 0.1 | 6.9 | 8.4 | 8.7 | 5.2 | 80 | 176 |
| C14 | 5.4 | 4.73 | 17.9 | 43.9 | 93 | 37.9 | 40.8 | 127 | 36.9 | 2 | 11.4 | 9.5 | 0.09 | 7.4 | 8.8 | 9 | 5 | 88 | 166 |
| C16 | 6.1 | 4.78 | 17.2 | 43.4 | 94.2 | 35.9 | 38.2 | 153 | 38.1 | 2.3 | 11.4 | 9.2 | 0.1 | 6.5 | 8.8 | 9 | 3.6 | 92 | 176 |
| C18 | 7.4 | 4.88 | 18.6 | 45 | 92.2 | 38.1 | 41.3 | 145 | 30.8 | 2.3 | 10.6 | 9.1 | 0.1 | 6.8 | 8.5 | 8.8 | 5.2 | 90 | 168 |
| C20 | 7 | 5.25 | 19.2 | 47 | 89.4 | 36.5 | 40.8 | 241 | 26.9 | 1.9 | 11 | 9 | 0.16 | 6.6 | 8.4 | 8.7 | 4.6 | 88 | 168 |
| C15 | 4.8 | 4.86 | 18.3 | 45.6 | 93.8 | 37.8 | 40.2 | 144 | 28.3 | 1.4 | 12.3 | 9.6 | 0.1 | 7.1 | 9.7 | 9.6 | 3.6 | 88 | 164 |
| C17 | 6.7 | 5.44 | 19.6 | 47.8 | 87.9 | 36.1 | 41.1 | 193 | 37.4 | 2.5 | 11.3 | 9.3 | 0.13 | 6.8 | 8.6 | 8.9 | 4.6 | 86 | 174 |
| C21 | 6.9 | 4.82 | 18.2 | 44.6 | 92.5 | 37.8 | 40.9 | 138 | 23 | 1.6 | 11.1 | 9.3 | 0.09 | 6.6 | 8.6 | 8.9 | 4.6 | 90 | 192 |
| C22 | 7.1 | 5.08 | 18 | 44.7 | 88 | 35.5 | 40.3 | 191 | 38.7 | 2.8 | 11.4 | 9.2 | 0.13 | 6.7 | 8.4 | 8.6 | 5 | 86 | 176 |
| rC28 | 5.8 | 5.58 | 17.2 | 45.9 | 82.1 | 31.3 | 37.4 | 226 | 43 | 2.5 | 10.9 | 8.3 | 0.16 | 7 | 8.5 | 8.8 | 4.9 | 89 | 132 |
| rC31 | 5.7 | 6.46 | 17.4 | 49.3 | 76.2 | 27 | 35.5 | 206 | 45.8 | 2.6 | 11.1 | 8.3 | 0.13 | 6.3 | 8.5 | 8.7 | 4.5 | 83 | 145 |
| rC41 | 5.4 | 5.75 | 16.2 | 45 | 78.5 | 28.2 | 35.9 | 204 | 30.2 | 1.6 | 11.3 | 8.2 | 0.14 | 6.6 | 8.3 | 8.6 | 4.7 | 86 | 136 |
| rC46 | 4.1 | 5.77 | 15.6 | 44.3 | 76.7 | 26.9 | 35.1 | 191 | 43 | 1.8 | 10.7 | 8.3 | 0.13 | 6.6 | 8 | 8.4 | 4.5 | 83 | 128 |
| rC47 | 6 | 5.53 | 12 | 36.8 | 66.5 | 21.8 | 32.8 | 223 | 17.5 | 1.1 | 12.9 | 8.1 | 0.16 | 7.2 | 8.4 | 8.6 | 5.6 | 74 | 140 |
| rC48 | 4.7 | 5.2 | 15.7 | 44 | 84.5 | 30.2 | 35.8 | 184 | 42.6 | 2 | 10.3 | 8.2 | 0.13 | 7.1 | 8.4 | 8.7 | 5.2 | 93 | 145 |
| rC51 | 6.6 | 5.69 | 16.2 | 45.1 | 79.2 | 28.4 | 35.9 | 165 | 25.6 | 1.7 | 10.3 | 8.1 | 0.11 | 7 | 8.5 | 8.7 | 4.7 | 89 | 135 |
| rC52 | 4 | 5.25 | 14.6 | 41.3 | 78.8 | 27.9 | 35.4 | 161 | 39.4 | 1.6 | 10.7 | 8.3 | 0.12 | 7.5 | 8.1 | 8.5 | 5.7 | 86 | 149 |
| rC59 | 5.3 | 4.98 | 14.9 | 43.1 | 86.6 | 30 | 34.7 | 173 | 43.2 | 2.3 | 10.1 | 8 | 0.12 | 6.8 | 8.2 | 8.6 | 5.1 | 97 | 137 |
| rC61 | 6.3 | 6.05 | 16.6 | 46.6 | 77.1 | 27.5 | 35.9 | 230 | 35.3 | 2.2 | 10.7 | 8.1 | 0.16 | 6.9 | 8.2 | 8.5 | 5.1 | 85 | 146 |
| rC68 | 4 | 5.39 | 15.6 | 43.6 | 80.9 | 29 | 35.9 | 170 | 44.6 | 1.8 | 10.6 | 8.2 | 0.12 | 7.1 | 8.4 | 8.7 | 5.6 | 90 | 141 |
| rC69 | 4.7 | 5.59 | 16.4 | 45.8 | 81.9 | 29.4 | 35.9 | 205 | 32.9 | 1.6 | 10.4 | 8.1 | 0.14 | 7 | 8.3 | 8.6 | 5.1 | 92 | 143 |
| rC71 | 6.2 | 5.74 | 15.7 | 45.2 | 78.7 | 27.4 | 34.9 | 168 | 44.4 | 2.7 | 11 | 8.2 | 0.12 | 7.1 | 8.1 | 8.5 | 5.4 | 87 | 128 | wherein
- WBC is the white blood cell count (k/ml)
- RBC is the red blood cell count.(M/ml)
- Hb is the hemoglobin content (g/dl)
- HCT is the hematocrit; volume percentage of erythrocytes (%)
- MCV is the mean cell volume of erythrocytes (fl($\mu^3$))
- MCH is the mean cell hemoglobin content (pg)
- MCHC is the mean cell hemoglobin concentration (g/dl)
- PLT is platelet count (k/ml)
- LYM is the ratio of the number of lymphocytes to the number of leukocytes (%)
- LYC is the lymphocyte count (k/ml)
- RDW is red blood cell size distribution width
- RDS is the red blood cell size distribution skewness
- PCT is the platelet crit; volume percentage of platelets in whole blood (%)
- MPV is the mean platelet volume (fl($\mu^3$))
- PDW is the platelet size distribution width.
- PDS is the platelet size distribution skewness.
- MP is the most frequent platelet volume (fl($\mu^3$))
- MR is the most frequent red blood cell volume (fl($\mu^3$))
- MW is the most frequent white blood cell volume. (fl($\mu^3$))

A test set of the same data was carried out with other patients of the same character as set forth in the preceding tables in order to evaluate the predictive capabilities of the analytic model.

TABLE 2

Test set

| Patient code | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| A2C3 | 10.4 | 5.48 | 15.8 | 45.9 | 83.9 | 28.8 | 34.4 | 242 | 20 | 1 | 10.6 | 8.1 | 0.16 | 6.5 | 8.2 | 8.5 | 5 | 93 | 134 |
| A3C3 | 8.2 | 4.93 | 14.8 | 43.2 | 87.7 | 30 | 34.3 | 253 | 30.2 | 2.5 | 11.2 | 8.1 | 0.171 | 6.8 | 8.2 | 8.5 | 5.4 | 98 | 151 |
| A3K3 | 6.9 | 5.33 | 16.1 | 44 | 82.9 | 30.3 | 36.6 | 139 | 37.4 | 2.6 | 8.7 | 8 | 0.096 | 6.9 | 8.7 | 8.9 | 4.4 | 93 | 147 |
| A2I3 | 5.8 | 5.82 | 18 | 50 | 85.9 | 31 | 36.1 | 158 | 27.8 | 1.6 | 10.9 | 8.2 | 0.11 | 7 | 8.4 | 8.7 | 5.6 | 95 | 139 |
| Amlgm5 | 4.6 | 4.43 | 15.7 | 42.2 | 95.3 | 35.5 | 37.3 | 166 | 33.8 | 1.6 | 10 | 9.1 | 0.11 | 6.8 | 8.5 | 8.8 | 5.8 | 94 | 168 |
| Amlgm12 | 7.8 | 4.36 | 13.9 | 38 | 87.1 | 31.9 | 36.6 | 136 | 30.1 | 2.4 | 11.9 | 9.3 | 0.1 | 7.2 | 8.4 | 8.7 | 6.2 | 84 | 158 |
| Amlgm21 | 3.9 | 5.3 | 17.1 | 48.2 | 90.8 | 32.4 | 35.6 | 127 | 42.5 | 1.6 | 10 | 9.2 | 0.09 | 6.8 | 8.3 | 8.7 | 5.4 | 88 | 180 |
| Amlgm22 | 4.7 | 4.83 | 17.2 | 48.2 | 99.7 | 35.5 | 35.5 | 173 | 40.9 | 1.9 | 10.8 | 9.1 | 0.12 | 7.2 | 8.5 | 8.8 | 6.2 | 100 | 182 |
| OrgSolv75 | 6.5 | 4.55 | 15.7 | 41.1 | 90.3 | 34.5 | 38.2 | 286 | 33.9 | 2.2 | 9.2 | 8.6 | 0.166 | 5.8 | 8.7 | 8.9 | 4.3 | 94 | 138 |
| OrgSolv97 | 3.2 | 5.3 | 16.5 | 48.9 | 91.4 | 30.9 | 33.8 | 329 | 55 | 1.8 | 11.7 | 9.8 | 0.248 | 7.5 | 9.5 | 9.6 | 6.2 | 84 | 94 |
| OrgSolv69 | 5.9 | 4.85 | 16.6 | 41.5 | 85.5 | 34.1 | 39.9 | 273 | 42.3 | 2.6 | 10.7 | 9 | 0.174 | 6.4 | 9.5 | 9.6 | 4.7 | 85 | 85 |
| OrgSolv83 | 3.8 | 4.8 | 15.6 | 46.8 | 96.8 | 32.3 | 33.4 | 270 | 41.3 | 1.6 | 10.5 | 9.5 | 0.177 | 6.5 | 9.2 | 9.2 | 5.3 | 91 | 105 |
| OrgSolv87 | 6.1 | 5.6 | 18.6 | 55.1 | 97.6 | 32.8 | 33.6 | 287 | 31.2 | 1.9 | 10.3 | 9.5 | 0.179 | 6.2 | 9.6 | 9.6 | 4.9 | 92 | 147 |
| Acryl3 | 4.1 | 4.45 | 13.5 | 41 | 92 | 30.4 | 33.1 | 30.7 | 41.9 | 1.7 | 9.4 | 8.9 | 0.174 | 5.6 | 10.6 | 10.5 | 3 | 92 | 84 |
| Acryl21 | 4.4 | 4.59 | 14.3 | 43.3 | 94.4 | 31.5 | 33.1 | 307 | 43.2 | 2 | 10 | 9.2 | 0.197 | 6.4 | 10.4 | 10.3 | 3.9 | 93 | 83 |
| Acryl43 | 5.1 | 4.38 | 13.4 | 40.5 | 92.5 | 30.6 | 33.1 | 367 | 26.7 | 1.4 | 8.7 | 9 | 0.222 | 6 | 10.1 | 10 | 3.1 | 93 | 151 |

TABLE 2-continued

Test set

| Patient code | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| Acryl7 | 5.4 | 5.13 | 15 | 46.4 | 90.4 | 29.4 | 32.5 | 310 | 42.8 | 2.3 | 10.1 | 9.1 | 0.195 | 6.2 | 10.5 | 10.3 | 3.1 | 89 | 89 |
| Acryl40 | 4.3 | 4.17 | 12.7 | 39.3 | 94 | 30.5 | 32.4 | 210 | 39.7 | 1.7 | 8.7 | 9 | 0.13 | 6.2 | 10.6 | 10.4 | 3 | 94 | 85 |
| aC6 | 5.8 | 4.78 | 12.4 | 40.4 | 84.6 | 25.9 | 30.7 | 199 | 35.7 | 2.1 | 10.8 | 9.2 | 0.15 | 7.3 | 8.4 | 8.7 | 5.6 | 82 | 150 |
| C19 | 7.8 | 4.61 | 17.8 | 43.2 | 93.8 | 38.7 | 41.2 | 177 | 25.6 | 2 | 11.2 | 9.2 | 0.12 | 6.8 | 8.6 | 8.8 | 5.2 | 92 | 166 |
| C12 | 5.1 | 5.04 | 17.3 | 43.4 | 86.3 | 34.3 | 39.8 | 150 | 41.4 | 2.1 | 12 | 9.5 | 0.11 | 7.5 | 8.8 | 8.9 | 5.2 | 82 | 162 |
| rC73 | 5.2 | 5.28 | 15.5 | 42.9 | 81.3 | 29.3 | 36.1 | 181 | 36.3 | 1.9 | 11 | 8.1 | 0.11 | 6.1 | 8.1 | 8.4 | 4.7 | 90 | 141 |
| rC81 | 5.1 | 5.18 | 15.5 | 43.3 | 83.5 | 30 | 35.9 | 222 | 36.4 | 1.8 | 10.4 | 8 | 0.14 | 6.4 | 8.3 | 8.6 | 4.4 | 92 | 135 |

The above blood cell analyses are copied from Excel® into Matlab® for Windows™, version 4.0, sold by MathWorks, Inc., Natick, Mass., and autoscaled there using the following routine in Matlab® for Windows™. The table of data is designated "x" and the code for autoscaling is—

Function i=autosc(x)

[m,n]=size(x);

i=x./(ones(m,1)*std(x));

i=i-ones(m,1 )*mean(i); end

The next step is the orthogonalization of the matrix. The autoscaled data is subjected to the singular value decomposition.

[U,S,V]=svd(autoscaled data matrix)

which is a command in Matlab® for Window.™ In order to produce the input data, a multiplication U times (*) S is carried out in Matlab® for Window.™ The orthogonalized matrix comprises the input data ("q") for the artificial neural network.

The following table 3 is the output data corresponding to the input data ("q") .

TABLE 3

| Patient code | Heart | Amalgam | OrgSolv | Acryl | Controls |
|---|---|---|---|---|---|
| A1A3 | 1 | 0 | 0 | 0 | 0 |
| A1B3 | 1 | 0 | 0 | 0 | 0 |
| A1G3 | 1 | 0 | 0 | 0 | 0 |
| A2A3 | 1 | 0 | 0 | 0 | 0 |
| A2D3 | 1 | 0 | 0 | 0 | 0 |
| A2E3 | 1 | 0 | 0 | 0 | 0 |
| A2G3 | 1 | 0 | 0 | 0 | 0 |
| A2H3 | 1 | 0 | 0 | 0 | 0 |
| A2J3 | 1 | 0 | 0 | 0 | 0 |
| A2K3 | 1 | 0 | 0 | 0 | 0 |
| A2L3 | 1 | 0 | 0 | 0 | 0 |
| A3B3 | 1 | 0 | 0 | 0 | 0 |
| A3D3 | 1 | 0 | 0 | 0 | 0 |
| A3E3 | 1 | 0 | 0 | 0 | 0 |
| A3F3 | 1 | 0 | 0 | 0 | 0 |
| A3G3 | 1 | 0 | 0 | 0 | 0 |
| A3H3 | 1 | 0 | 0 | 0 | 0 |
| A3I3 | 1 | 0 | 0 | 0 | 0 |
| A3M3 | 1 | 0 | 0 | 0 | 0 |
| Amlgm1 | 0 | 1 | 0 | 0 | 0 |
| Amlgm2 | 0 | 1 | 0 | 0 | 0 |
| Amlgm3 | 0 | 1 | 0 | 0 | 0 |
| Amlgm4 | 0 | 1 | 0 | 0 | 0 |
| Amlgm6 | 0 | 1 | 0 | 0 | 0 |
| Amlgm7 | 0 | 1 | 0 | 0 | 0 |
| Amlgm8 | 0 | 1 | 0 | 0 | 0 |
| Amlgm9 | 0 | 1 | 0 | 0 | 0 |
| Amlgm10 | 0 | 1 | 0 | 0 | 0 |
| Amlgm10 | 0 | 1 | 0 | 0 | 0 |
| Amlgm13 | 0 | 1 | 0 | 0 | 0 |

TABLE 3-continued

| Patient code | Heart | Amalgam | OrgSolv | Acryl | Controls |
|---|---|---|---|---|---|
| Amlgm14 | 0 | 1 | 0 | 0 | 0 |
| Amlgm15 | 0 | 1 | 0 | 0 | 0 |
| Amlgm16 | 0 | 1 | 0 | 0 | 0 |
| Amlgm17 | 0 | 1 | 0 | 0 | 0 |
| Amlgm20 | 0 | 1 | 0 | 0 | 0 |
| Amlgm23 | 0 | 1 | 0 | 0 | 0 |
| Amlgm24 | 0 | 1 | 0 | 0 | 0 |
| Amlgm25 | 0 | 1 | 0 | 0 | 0 |
| OrgSolv73 | 0 | 0 | 1 | 0 | 0 |
| OrgSolv74 | 0 | 0 | 1 | 0 | 0 |
| OrgSolv98 | 0 | 0 | 1 | 0 | 0 |
| OrgSolv99 | 0 | 0 | 1 | 0 | 0 |
| OrgSolv67 | 0 | 0 | 1 | 0 | 0 |
| OrgSolv68 | 0 | a | 1 | 0 | 0 |
| OrgSolv84 | 0 | 0 | 1 | 0 | 0 |
| OrgSolv85 | 0 | 0 | 1 | 0 | 0 |
| OrgSolv94 | 0 | 0 | 1 | 0 | 0 |
| OrgSolv95 | 0 | 0 | 1 | 0 | 0 |
| OrgSolv96 | 0 | 0 | 1 | 0 | 0 |
| OrgSolv70 | 0 | 0 | 1 | 0 | 0 |
| OrgSolv71 | 0 | 0 | 1 | 0 | 0 |
| OrgSolv72 | 0 | 0 | 1 | 0 | 0 |
| OrgSolv64 | 0 | 0 | 1 | 0 | 0 |
| OrgSolv65 | 0 | 0 | 1 | 0 | 0 |
| OrgSolv66 | 0 | 0 | 1 | 0 | 0 |
| OrgSolv91 | 0 | 0 | 1 | 0 | 0 |
| OrgSolv92 | 0 | 0 | 1 | 0 | 0 |
| OrgSolv93 | 0 | 0 | 1 | 0 | 0 |
| OrgSolv88 | 0 | 0 | 1 | 0 | 0 |
| OrgSolv89 | 0 | 0 | 1 | 0 | 0 |
| OrgSolv90 | 0 | 0 | 1 | 0 | 0 |
| OrgSolv61 | 0 | 0 | 1 | 0 | 0 |
| OrgSolv62 | 0 | 0 | 1 | 0 | 0 |
| OrgSolv63 | 0 | 0 | 1 | 0 | 0 |
| OrgSolv76 | 0 | 0 | 1 | 0 | 0 |
| OrgSolv77 | 0 | 0 | 1 | 0 | 0 |
| OrgSolv78 | 0 | 0 | 1 | 0 | 0 |
| OrgSolv60 | 0 | 0 | 1 | 0 | 0 |
| OrgSolv79 | 0 | 0 | 1 | 0 | 0 |
| OrgSolv80 | 0 | 0 | 1 | 0 | 0 |
| OrgSolv81 | 0 | 0 | 1 | 0 | 0 |
| OrgSolv82 | 0 | 0 | 1 | 0 | 0 |
| OrgSolv86 | 0 | 0 | 1 | 0 | 0 |
| Acryl10 | 0 | 0 | 0 | 1 | 0 |
| Acryl12 | 0 | 0 | 0 | 1 | 0 |
| Acryl13 | 0 | 0 | 0 | 1 | 0 |
| Acryl1 | 0 | 0 | 0 | 1 | 0 |
| Acryl2 | 0 | 0 | 0 | 1 | 0 |
| Acryl22 | 0 | 0 | 0 | 1 | 0 |
| Acryl24 | 0 | 0 | 0 | 1 | 0 |
| Acryl25 | 0 | 0 | 0 | 1 | 0 |
| Acryl26 | 0 | 0 | 0 | 1 | 0 |
| Acryl4 | 0 | 0 | 0 | 1 | 0 |
| Acryl5 | 0 | 0 | 0 | 1 | 0 |
| Acryl6 | 0 | 0 | 0 | 1 | 0 |
| Acryl42 | 0 | 0 | 0 | 1 | 0 |
| Acryl8 | 0 | 0 | 0 | 1 | 0 |
| Acryl9 | 0 | 0 | 0 | 1 | 0 |

TABLE 3-continued

| Patient code | Heart | Amalgam | OrgSolv | Acryl | Controls |
|---|---|---|---|---|---|
| Acryl14 | 0 | 0 | 0 | 1 | 0 |
| Acryl16 | 0 | 0 | 0 | 1 | 0 |
| Acryl17 | 0 | 0 | 0 | 1 | 0 |
| Acryl30 | 0 | 0 | 0 | 1 | 0 |
| Acryl31 | 0 | 0 | 0 | 1 | 0 |
| Acryl33 | 0 | 0 | 0 | 1 | 0 |
| Acryl38 | 0 | 0 | 0 | 1 | 0 |
| Acryl39 | 0 | 0 | 0 | 1 | 0 |
| Acryl18 | 0 | 0 | 0 | 1 | 0 |
| Acryl19 | 0 | 0 | 0 | 1 | 0 |
| Acryl20 | 0 | 0 | 0 | 1 | 0 |
| aC1 | 0 | 0 | 0 | 0 | 1 |
| aC2 | 0 | 0 | 0 | 0 | 1 |
| aC3 | 0 | 0 | 0 | 0 | 1 |
| aC4 | 0 | 0 | 0 | 1 | 1 |
| aC5 | 0 | 0 | 0 | 0 | 1 |
| aC7 | 0 | 0 | 0 | 0 | 1 |
| aC8 | 0 | 0 | 0 | 0 | 1 |
| C13 | 0 | 0 | 0 | 0 | 1 |
| C14 | 0 | 0 | 0 | 0 | 1 |
| C16 | 0 | 0 | 0 | 0 | 1 |
| C18 | 0 | 0 | 0 | 0 | 1 |
| C20 | 0 | 0 | 0 | 0 | 1 |
| C15 | 0 | 0 | 0 | 0 | 1 |
| C17 | 0 | 0 | 0 | 0 | 1 |
| C21 | 0 | 0 | 0 | 0 | 1 |
| C22 | 0 | 0 | 0 | 0 | 1 |
| rC28 | 0 | 0 | 0 | 0 | 1 |
| rC31 | 0 | 0 | 0 | 0 | 1 |
| rC41 | 0 | 0 | 0 | 0 | 1 |
| rC46 | 0 | 0 | 0 | 0 | 1 |
| rC47 | 0 | 0 | 0 | 0 | 1 |
| rC48 | 0 | 0 | 0 | 0 | 1 |
| rC51 | 0 | 0 | 0 | 0 | 1 |
| rC52 | 0 | 0 | 0 | 0 | 1 |
| rC59 | 0 | 0 | 0 | 0 | 1 |
| rC61 | 0 | 0 | 0 | 0 | 1 |
| rC68 | 0 | 0 | 0 | 0 | 1 |
| rC69 | 0 | 0 | 0 | 0 | 1 |
| rC71 | 0 | 0 | 0 | 0 | 1 |

TABLE 4

Test Set Data:

| | | | | | |
|---|---|---|---|---|---|
| Acryl2 | 0 | 0 | 0 | 1 | 0 |
| Acryl22 | 0 | 0 | 0 | 1 | 0 |
| Acryl24 | 0 | 0 | 0 | 1 | 0 |
| Acryl25 | 0 | 0 | 0 | 1 | 0 |
| Acryl26 | 0 | 0 | 0 | 1 | 0 |
| Acryl4 | 0 | 0 | 0 | 1 | 0 |
| Acryl5 | 0 | 0 | 0 | 1 | 0 |
| Acryl6 | 0 | 0 | 0 | 1 | 0 |
| Acryl42 | 0 | 0 | 0 | 1 | 0 |
| Acryl8 | 0 | 0 | 0 | 1 | 0 |
| Acryl9 | 0 | 0 | 0 | 1 | 0 |
| Acryl14 | 0 | 0 | 0 | 1 | 0 |
| Acryl16 | 0 | 0 | 0 | 1 | 0 |
| Acryl17 | 0 | 0 | 0 | 1 | 0 |
| Acryl30 | 0 | 0 | 0 | 1 | 0 |
| Acryl31 | 0 | 0 | 0 | 1 | 0 |
| Acryl33 | 0 | 0 | 0 | 1 | 0 |
| Acryl38 | 0 | 0 | 0 | 1 | 0 |
| Acryl39 | 0 | 0 | 0 | 1 | 0 |
| Acryl18 | 0 | 0 | 0 | 1 | 0 |
| Acryl19 | 0 | 0 | 0 | 1 | 0 |
| Acryl20 | 0 | 0 | 0 | 1 | 0 |
| aC1 | 0 | 0 | 0 | 0 | 1 |
| aC2 | 0 | 0 | 0 | 0 | 1 |
| aC3 | 0 | 0 | 0 | 0 | 1 |
| aC4 | 0 | 0 | 0 | 0 | 1 |
| aC5 | 0 | 0 | 0 | 0 | 1 |
| aC7 | 0 | 0 | 0 | 0 | 1 |
| aC8 | 0 | 0 | 0 | 0 | 1 |

TABLE 4-continued

Test Set Data:

| | | | | | |
|---|---|---|---|---|---|
| C13 | 0 | 0 | 0 | 0 | 1 |
| C14 | 0 | 0 | 0 | 0 | 1 |
| C16 | 0 | 0 | 0 | 0 | 1 |
| C18 | 0 | 0 | 0 | 0 | 1 |
| C20 | 0 | 0 | 0 | 0 | 1 |
| C15 | 0 | 0 | 0 | 0 | 1 |
| C17 | 0 | 0 | 0 | 0 | 1 |
| C21 | 0 | 0 | 0 | 0 | 1 |
| C22 | 0 | 0 | 0 | 0 | 1 |
| rC28 | 0 | 0 | 0 | 0 | 1 |
| rC31 | 0 | 0 | 0 | 0 | 1 |
| rC41 | 0 | 0 | 0 | 0 | 1 |
| rC46 | 0 | 0 | 0 | 0 | 1 |
| rC47 | 0 | 0 | 0 | 0 | 1 |
| rC48 | 0 | 0 | 0 | 0 | 1 |
| rC51 | 0 | 0 | 0 | 0 | 1 |
| rC52 | 0 | 0 | 0 | 0 | 1 |
| rC59 | 0 | 0 | 0 | 0 | 1 |
| rC61 | 0 | 0 | 0 | 0 | 1 |
| rC68 | 0 | 0 | 0 | 0 | 1 |
| rC69 | 0 | 0 | 0 | 0 | 1 |
| rC71 | 0 | 0 | 0 | 0 | 1 |
|  | 1 | 0 | 0 | 0 | 0 |
|  | 1 | 0 | 0 | 0 | 0 |
|  | 1 | 0 | 0 | 0 | 0 |
|  | 1 | 0 | 0 | 0 | 0 |
|  | 0 | 1 | 0 | 0 | 0 |
|  | 0 | 1 | 0 | 0 | 0 |
|  | 0 | 1 | 0 | 0 | 0 |
|  | 0 | 1 | 0 | 0 | 0 |
|  | 0 | 0 | 1 | 0 | 0 |
|  | 0 | 0 | 1 | 0 | 0 |
|  | 0 | 0 | 1 | 0 | 0 |
|  | 0 | 0 | 1 | 0 | 0 |
|  | 0 | 0 | 0 | 1 | 0 |
|  | 0 | 0 | 0 | 1 | 0 |
|  | 0 | 0 | 0 | 1 | 0 |
|  | 0 | 0 | 0 | 1 | 0 |
|  | 0 | 0 | 0 | 1 | 0 |
|  | 0 | 0 | 0 | 0 | 1 |
|  | 0 | 0 | 0 | 0 | 1 |
|  | 0 | 0 | 0 | 0 | 1 |
|  | 0 | 0 | 0 | 0 | 1 |
|  | 0 | 0 | 0 | 0 | 1 |

THE ARTIFICIAL NEURAL NETWORK

The artificial neural network is configured using Matlab® for Windows™, according to the number of input variables, which in the above case (Table 1) is 19, providing the number of input neurons.

The following program[2] is generated on a computer by Matlab® for Windows™ to configure the artificial neural network by inputting the first line with function and initff data:

[w1,b1,w2,b2]=initff(p,s1,f1,T,f2)

The arguments in the above equation for the above illustration are as follows:

w1 is the weight matrix for the hidden layer;

b1 is the vector of biases for the hidden layer;

w2 is the weight matrix for the output layer;

b2 is the vector of biases for the output layer;

p is the matrix of minimum and maximum values for input matrix;

s1 is the number of neurons in the hidden layer which is 40 in this case;

f1 is the transfer function for the hidden layer and in this case is called the hyperbolic tangent sigmoid function;

T is matrix of target vectors as set forth in Table 3 above; and f2 is the transfer function for the output layer, which in this case it is the logistic sigmoid function.

```
%INITFF Initialize feed-forward network up to 3 layers.
%
%   [W1,B1, ... ] = INITFF(P,S1,'F1', ... ,Sn,'Fn')
%   P - Rx2 matrix of input vectors.
%   Si - Size of ith layer.
%   Fi - Transfer function of the ith layer (string).
%   Returns:
%     Wi - Weight matrix of the ith layer.
%     Bi - Bias (column) vector of the ith layer.
%   [W1,B1, ... ] = INITFF(P,S1,'F1', ... T,'Fn')
%   T - SnxQ matrix of target vectors.
%   Returns weights and biases.
%   IMPORTANT: Each ith row of P must contain expected
%   min and max values for the ith input.
%
%   EXAMPLE: [W1,b1,W2,b2 = initff([0 10; -5 5],5,'tansig',3,'pure
%   p = [4; -1];
%   a = simuff(p,W1,b1,'tansig',W2,b2,'purelin')
%   See also NNINIT, BACKPROP, SIMUFF, TRAINBPX, TRAINLM
    if all([3 5 7] ~= nargin),error('Wrong number of input arguments'),
    end
[R,Q] = size(p);
if (Q < 2), error('P must contain at least two elements in each row.'),end
if nargin == 3
[S,Q] = size(s1);
if max(S,Q) > 1, s1 = S; end
[w1,b1] = feval(feval(f1,'init'),s1,p);
elseif nargin == 5
[w1,b1] = feval(feval(f1,'init'),s1,p);
x = ones(s1,1) * feval(f1,'output');
[S,Q] = size(s2);
if max(S,Q) > 1, s2 = S; end
[w2,b2] = feval(feval(f2,'init'),s2,x);
elseif nargin == 7
[w1,b1] = feval(feval(f1,'init'),s1,p);
x = ones(s1,1) * feval(f1,'output');
[w2,b2] = feval(feval(f2,'init'),s2,x);
x = ones(s2,1) * feval(f2,'output');
[S,Q] = size(s3);
if max(S,Q) > 1, s3 = S; end
[w3,b3] = feval(feval(f3,'init'),s3,x);
end
```

[2] written by Mark Beale, Dec. 15, 1993 and Copyright©1992-94 by the MathWorks, Inc. Revision: 1.1 Date: Jan. 11, 1994, 16:24:46.

The next step involves training the artificial neural network. Again, the computation is carried out in a computer using Matlab® for Windows™ through use of the program called "TrainBPX.M".[3] In this case, input is made to the equation—

[W1,B1,W2,B2, ... , TE,TR]=TRAINBPX(W1,B1,F1,W2,B2,F2, ... ,P,T,TP)

wherein

W1 on the left side of the equation is the initial weight matrix for the hidden layer and on the right side of the equation, the optimal weight matrix;

B1 on the left side of the equation is the initial vector of biases for the hidden layer and on the right of the equation is the optimal vector of biases for the hidden layer;

W2 on the left side is the initial weight matrix for the output layer and on the right side is the optimal weight matrix for the output layer;

B2 on the left side is the vector of biases for the output layer and on the right side is the optimum vector of biases for the output layer;

P is the matrix of input vectors as recited in Table 1;

TE is the actual number of training passes or epics (in this case 5000);

TR is the training record which is the stored error of pass through the network;

F1 is the transfer function for the hidden layer and in this case is called the hyperbolic tangent sigmoid function;

T is matrix of target vectors as set forth in Table 3 above;

F2 is the transfer function for the output layer, which in this case it is the logistic sigmoid function; and TP is an optional vector of training parameters.

[3] The program is indicated to be copyrighted by Mark Beale and by the MathWorks, Inc.

The Matlab® for Windows™ TrainBPX.M screen appears as:

```
"function [a,b,c,d,e,f,g,h] = trainbpx(i,j,k,l,m,n,o,p,q,r,s,t)
%TRAINBPX Train feed-forward network with fast backpropagation.
%
%   TRAINBPX can be called with 1, 2, or 3 sets of weights
%   and biases to train up to 3 layer feed-forward networks.
%
%   [W1,B1,W2,B2, ... ,TE,TR] = TRAINBPX(W1,B1,F1,W2,B2,
%   F2, ... ,P,T,TP)
%     Wi - Weight matrix for the ith layer.
%     Bi - Bias vector for the ith layer.
%     Fi - Transfer function (string) for the ith layer.
%     P - RxQ matrix of input vectors.
%     T - SxQ matrix of target vectors.
%     TP - Training parameters (optional).
%   Returns new weights and biases and
%     Wi - new weights.
%     Bi - new biases.
%     TE - the actual number of epochs trained.
%     TR - training record: [row of errors]
%
%   Training parameters are:
%     TP(1) - Epochs between updating display, default = 25.
%     TP(2) - Maximum number of epochs to train, default = 1000.
%     TP(3) - Sum-squared error goal, default = 0.02.
%     TP(4) - Learning rate, 0.01.
%     TP(5) - Learning rate increase, default = 1.05.
%     TP(6) - Learning rate decrease, default = 0.7.
%     TP(7) - Momentum constant, default = 0.9.
%     TP(8) - Maximum error ratio, default = 1.04.
%   Missing parameters and NaN's are replaced with defaults.
%
%   See also NNTRAIN, BACKPROP, INITFF, SIMFF, TRAINBP,
%   TRAINLM.
% Mark Beale, 9-2-92
% Revised 12-15-93, MB.
% Copyright (c) 1992-94 by the MathWorks, Inc.
% $Revision: 1.1 $ $Date: 1994/01/11 16:30:06 $
if all([5 6 8 9 11 12] ~= nargin),error('Wrong number of input arguments'),end
if nargin == 5
[a,b,c,d] = tbpx1(i,j,k,l,m);
elseif nargin == 6
[a,b,c,d] = tbpx1(i,j,k,l,m,n);
elseif nargin == 8
[a,b,c,d,e,f] = tbpx2(i,j,k,l,m,n,o,p);
elseif nargin == 9
[a,b,c,d,e,f] = tbpx2(i,j,k,l,m,n,o,p,q);
elseif nargin == 11
[a,b,c,d,e,f,g,h] = tbpx3(i,j,k,l,m,n,o,p,q,r,s);
elseif nargin == 12
[a,b,c,d,e,f,g,h] = tbpx3(i,j,k,l,m,n,o,p,q,r,s,t);
end"
```

The next step involves using the trained artificial neural network and the analytic model thereof to obtain a diagnosis for a patient or patients that have not previously been diagnosed. This is done by the following sequence:

withdrawing from a new patient that has not been diagnosed for such disorder, a sample or samples of a kind taken from said reference patients and subjecting said diagnostic sample to said clinical testing to obtain new numerical data;

automatically scaling in the computer the new data to the data derived from the reference patients;

feeding the scaled new data to the trained artificial neural network and the analytic model thereof, and automatically obtaining a diagnosis as to the new patient with respect to such disorders.

Again, the computation is carried out on a computer using Matlab® for Windows™ through use of the program called "Simuff..M".[4] In this case, input is made to the equation—

[A]=SIMUFF(P, W1,B1,'F1',W2,B2,'F2')

wherein

A is the result from the layer of output neurons, i.e. the prediction;

W1 is the optimal weight matrix;

B1 is the optimal vector of biases for the hidden layer;

W2 is the optimal weight matrix for the output layer;

B2 is the optimum vector of biases for the output layer;

P is the matrix of input vectors obtained from undiagnosed patients;

F1 is the transfer function for the hidden layer and in this case is called the hyperbolic tangent sigmoid function;

F2 is the transfer function for the output layer, which in this case it is the logistic sigmoid function Simuff..M appears on the computer screen as:

```
"function [a1,a2,a3] = simuff(p,w1,b1,f1,w2,b2,f2,w3,b3,f3)
%SIMUFF Simulate feed-forward network.
%
%   SIMUFF will simulate networks with up to 3 layers.
%
%   SIMUFF(P,W1,B1,'F1', ... ,Wn,Bn,'Fn')
%     P - Matrix of input (column) vectors.
%     Wi - Weight matrix of the ith layer.
%     Bi - Bias (column) vector of the ith layer.
%     Fi - Transfer function of the ith layer (string).
%   Returns output of nth layer.
%
%   [A1,A2, ... ] =SIMUFF(P,W1,B1,'F1', ... ,Wn,Bn,'Fn')
%   Returns:
%     Ai - Output of the ith layer.
%
%   EXAMPLE: [w1,b1,w2,b2] = initff([0 10; -5 5],3,'tansig',2,
%     'purelin');
%         p = [2; -3];
%         a = simuff(p,w1,b1,'tansig',w2,b2,'purelin')
%   See also NNSIM, BACKPROP, INITFF, TRAINBPX, TRAINLM.
if all([4 7 10] = nargin),error('Wrong number of input arguments'),end
if nargin == 4
   a1 = feval(f1,w1*p,b1);
elseif nargin == 7
   a1 = feval(f1,w1*p,b1);
   a2 = feval(f2,w2*a1,b2);
   if nargout <= 1, a1 = a2; end
elseif nargin == 10
   a1 = feval(f1,w1*p,b1);
   a2 = feval(f2,w2*a1,b2);
   a3 = feval(f3,w3*a2,b3);
   if nargout <= 1, a1 = a3; end
end
```

[4] The program is indicated to be copyrighted by Mark Beale and by the MathWorks, Inc.

The validity of the above described artificial neural network analytic model can be tested and quantified using a standard procedure in multivariate modeling, namely that of an independent test set comprising data from a group of patients that have been previously diagnosed, described in table 4, and have had samples withdrawn of a kind taken from said reference patients. The diagnostic sample is subjected to said clinical testing to obtain new numerical data, described in table 2, automatically scaling in the computer the new data to the data derived from the reference patients, feeding the scaled new data to the trained artificial neural network and the analytic model thereof, and automatically obtaining a diagnosis as to the test-set patients with respect to such disorders.

The diagnosis predicted by the artificial neural network can be compared to the diagnosis previously obtained and one of a number of different measures of the validity of the artificial neural network and the analytic model thereof can be calculated as follows: Classification Success (%);

CS=100*(wrong classifications/classifications)

A typical value of CS for the artificial neural network is 92%.

As a final step in the process an approximate probability level, associated to the diagnosis of disorder via the above described artificial neural network, can be calculated electronically in the computer using a variant of the Students t-test to obtain the probability level.

The calculation of the probability level is done in a three step process. The first step involves building a PLS-Discriminant Analysis model (M. Sjöström, S. Wold and B. Söderström, PLS Discriminant Plots, in "Pattern Recognition in Practice II" (1986), E. S. Gelsema and L. N. Kanal, Eds., Elsevier Science Publishers (North-Holland), pages 461–470) for each disorder group, using the aforementioned reference groups. The second step uses the above described artificial neural network analytic model to select the matching disorder for the unknown and undiagnosed patient and the associated PLS-Discriminant Analysis model. The third and final step uses the selected PLS-Discriminant Analysis model and the above mentioned Students t-test to ascertain the probability level of the diagnosis.

In the first step, a PLS-Discriminant Analysis model for each reference group is developed, separately for each reference group. Again, the computation is carried out using Matlab® for Windows™ through use of the program called "PLS.M".[5] In this case, input is made to the equation;

[P,Q,W,T,U,b,ssqdif]=pls(x,y,lv)

wherein

P is the matrix of x-loadings;

Q is the matrix of y-loadings;

W is the matrix of weights;

T is the matrix of x-scores;

U is the matrix of y-scores;

b is the vector of regression coefficients between x and y;

ssqdif is the variance contained in each latent variable;

x is the matrix of input vectors, comprised of data from one reference group and one group of healthy patients, all as recited in table 5;

y is the matrix of target vectors as in table 6;

lv is the total number of latent variables to be calculated function [P,Q,W,T,U,b,ssqdif]=pls(x,y,lv)

[5] The computer screen indicates that the program is the copyright of Barry M. Wise, 1991.

```
% This PLS program calculates the P, Q, W, T, and U matrices
% for the given x and y blocks and the number of latent
% variables specified. It also outputs the fraction of
% variance used in the x and y matrices.
% Input format is as follows:
% function [P,Q,W,T,U,b,ssqdif] = pls(x,y,lv);
[mx,nx] = size(x);
[my,ny] = size(y);
if nx < lv
error('No. of LVs must be <= no. of x-block variables')
end
P = zeros(nx,lv);
Q = zeros(ny,lv);
W = zeros(nx,lv);
T = zeros(mx,lv);
U = zeros(my,lv);
b = zeros(1,lv);
ssq = zeros(lv,2);
ssqx = 0;
for I = 1:nx
    ssqx = ssqx + sum(x(:,I).^2);
end
ssqy = sum(sum(y.^2)');
for I = 1:lv
    [p,q,w,t,u] = plsnipal(x,y);
    b(1,I) = u'*t/(t'*t);
    x = x - t*p';
    y = y - b(1,I)*t*q';
    ssq(I,1) = (sum(sum(x.^2)'))*100/ssqx;
    ssq(I,2) = (sum(sum(y.^2)'))*100/ssqy;
    T(:,I) = t(:,1);
    U(:,I) = u(:,1);
    P(:,I) = p(:,1);
    W(:,I) = w(:,1);
    Q(:,I) = q(:,1);
end
ssqdif = zeros(lv,2);
ssqdif(1,1) = 100 - ssq(1,1);
ssqdif(1,2) = 100 - ssq(1,2);
for I = 2:lv
    for j = 1:2
        ssqdif(I,j) = -ssq(I,j) + ssq(I-1,j);
    end
end
disp(' ')
disp('   Percent Variance Captured by PLS Model')
disp(' ')
disp('       ----X-Block----    ----Y-Block----')
disp('  LV#  This LV   Total   This LV   Total')
disp([(1:lv)'ssqdif(:,1) cumsum(ssqdif(:,1)) ssqdif(:,2) cumsum(ssqdif(:,2))])
```

TABLE 5

| Reference Patients | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| Amlgm1  | 12.5 | 4.35 | 17.4 | 45.1 | 103.7 | 40.1 | 38.7 | 193 | 22.5 | 2.8 | 11.1 | 9.2 | 0.13 | 6.6 | 8.6 | 8.8 | 5.3 | 102 | 176 |
| Amlgm2  | 5.9  | 4.2  | 13.4 | 39.7 | 94.4  | 31.9 | 33.8 | 135 | 38   | 2.3 | 10.8 | 9.3 | 0.1  | 7.7 | 9   | 9.2 | 5.8 | 92  | 154 |
| Amlgm3  | 8    | 4.24 | 13.7 | 40.6 | 95.6  | 32.2 | 33.7 | 150 | 33   | 2.6 | 10.8 | 9.1 | 0.12 | 7.7 | 8.7 | 8.9 | 6.5 | 96  | 158 |
| Amlgm4  | 6.7  | 5.07 | 19.1 | 46.5 | 96.6  | 37.1 | 41.2 | 191 | 37.1 | 2.5 | 10.7 | 9.2 | 0.12 | 6.5 | 8.6 | 8.8 | 5   | 90  | 174 |
| Amlgm6  | 6    | 4.25 | 14.4 | 39.6 | 93.2  | 34   | 36.4 | 112 | 35.1 | 2.1 | 9.8  | 9.2 | 0.08 | 7.4 | 9   | 9.2 | 6.2 | 92  | 170 |
| Amlgm7  | 7    | 4.55 | 15.5 | 41.9 | 92.1  | 34.1 | 37   | 149 | 26.8 | 1.9 | 9.8  | 9.1 | 0.11 | 7.6 | 8.7 | 8.8 | 6.2 | 92  | 176 |
| Amlgm8  | 14.2 | 4.81 | 17   | 45.6 | 94.9  | 35.4 | 37.4 | 169 | 21.5 | 3.1 | 10.5 | 9.4 | 0.12 | 7   | 8.6 | 8.8 | 5.8 | 92  | 172 |
| Amlgm9  | 8.3  | 4.35 | 15.3 | 41.7 | 95.7  | 35.1 | 36.6 | 159 | 38.6 | 3.2 | 10.6 | 9.4 | 0.11 | 7.2 | 8.4 | 8.6 | 5.6 | 92  | 166 |
| Amlgm10 | 8.2  | 5.44 | 18   | 49.3 | 90.7  | 33.1 | 36.5 | 147 | 33.3 | 2.7 | 11.1 | 9.3 | 0.11 | 7.2 | 8.6 | 8.8 | 6.4 | 88  | 168 |
| Amlgm11 | 10.6 | 4.58 | 16.3 | 44   | 96.1  | 35.7 | 37.2 | 166 | 33.3 | 3.5 | 10.1 | 9.2 | 0.12 | 7.1 | 8.5 | 8.8 | 6.2 | 94  | 162 |
| Amlgm13 | 6.2  | 4.38 | 14.3 | 39.1 | 89.3  | 32.6 | 36.5 | 169 | 41.1 | 2.5 | 11.8 | 9.4 | 0.13 | 7.4 | 8.6 | 8.8 | 6.2 | 86  | 160 |
| Amlgm14 | 6.1  | 4.86 | 17.1 | 46.2 | 95.3  | 35.2 | 36.9 | 146 | 40.9 | 2.5 | 10.3 | 9.2 | 0.11 | 7.2 | 8.8 | 9   | 5.2 | 92  | 166 |
| Amlgm15 | 8.8  | 4.85 | 17.3 | 48.8 | 100.5 | 35.7 | 35.5 | 170 | 28.4 | 2.5 | 10.7 | 9.2 | 0.11 | 6.7 | 8.5 | 8.8 | 5.2 | 98  | 166 |
| Amlgm16 | 5.8  | 3.87 | 13.3 | 37.7 | 97.2  | 34.4 | 35.4 | 158 | 36.4 | 2.1 | 9.8  | 9.1 | 0.11 | 7.1 | 8.9 | 9.1 | 6.4 | 96  | 162 |
| Amlgm17 | 5.6  | 5.21 | 16.5 | 48.8 | 93.8  | 31.8 | 33.9 | 221 | 25.6 | 1.4 | 11.2 | 9.3 | 0.15 | 6.8 | 8.9 | 9.1 | 4.6 | 90  | 160 |
| Amlgm20 | 5.6  | 4.89 | 15.7 | 44   | 89.9  | 32.1 | 35.7 | 163 | 24.9 | 1.3 | 10.6 | 9.2 | 0.12 | 7.2 | 8.4 | 8.7 | 6.4 | 88  | 160 |
| Amlgm23 | 5.1  | 4.15 | 11.7 | 38.4 | 92.6  | 28.1 | 30.4 | 201 | 35.5 | 1.8 | 10.8 | 9.2 | 0.14 | 7.2 | 8.4 | 8.7 | 5.4 | 90  | 152 |
| Amlgm24 | 7.2  | 5.13 | 13.2 | 43.8 | 85.5  | 25.6 | 30   | 240 | 20.1 | 1.4 | 11.9 | 9.3 | 0.17 | 7.1 | 8.5 | 8.7 | 5.8 | 84  | 154 |
| Amlgm25 | 6.8  | 4.41 | 12   | 38.6 | 87.6  | 27.2 | 31   | 233 | 28.6 | 1.9 | 10.8 | 9.2 | 0.17 | 7.2 | 7.9 | 8.3 | 6   | 86  | 150 |
| Healthy Patients | | | | | | | | | | | | | | | | | | | |
| aC1 | 5.5 | 4.53 | 11.5 | 37.8 | 83.6 | 25.4 | 30.4 | 180 | 35.7 | 2   | 11.5 | 9.3 | 0.12 | 6.8 | 8.1 | 8.5 | 5.4 | 82 | 144 |
| aC2 | 5.9 | 4.38 | 12.5 | 40.7 | 92.9 | 28.5 | 30.7 | 175 | 29.9 | 1.7 | 10.6 | 9.1 | 0.12 | 6.7 | 8.2 | 8.6 | 5   | 92 | 152 |
| aC3 | 3.9 | 4.59 | 12.8 | 41.4 | 90.2 | 27.9 | 30.9 | 153 | 41.7 | 1.6 | 10.4 | 9.1 | 0.1  | 6.5 | 8   | 8.4 | 5.2 | 90 | 150 |
| aC4 | 6.1 | 5.04 | 14.4 | 46   | 91.3 | 28.6 | 31.3 | 175 | 30.7 | 1.9 | 10.9 | 9.1 | 0.11 | 6.4 | 8.1 | 8.4 | 4.6 | 90 | 150 |
| aC5 | 6.3 | 4.94 | 14.1 | 44.9 | 90.8 | 28.5 | 31.4 | 178 | 39.7 | 2.5 | 11.1 | 9.3 | 0.13 | 7.5 | 8.5 | 8.8 | 5.8 | 88 | 154 |
| aC7 | 2.9 | 4.74 | 12.3 | 40.7 | 85.6 | 26   | 30.3 | 108 | 45.9 | 1.3 | 11   | 9.2 | 0.08 | 7.4 | 8.3 | 8.6 | 5.8 | 84 | 154 |
| aC8 | 5.2 | 5.27 | 14.4 | 45.7 | 86.8 | 27.3 | 31.9 | 143 | 34   | 1.8 | 11.6 | 9.2 | 0.11 | 7.5 | 8.5 | 8.8 | 5.8 | 84 | 148 |
| C13 | 4.3 | 5.09 | 16.7 | 43.2 | 84.9 | 32.8 | 38.7 | 147 | 34   | 1.4 | 11.9 | 9.4 | 0.1  | 6.9 | 8.4 | 8.7 | 5.2 | 80 | 176 |
| C14 | 5.4 | 4.73 | 17.9 | 43.9 | 93   | 37.9 | 40.8 | 127 | 36.9 | 2   | 11.4 | 9.5 | 0.09 | 7.4 | 8.8 | 9   | 5   | 88 | 166 |
| C16 | 6.1 | 4.78 | 17.2 | 43.4 | 94.2 | 35.9 | 38.2 | 153 | 38.1 | 2.3 | 11.4 | 9.2 | 0.1  | 6.5 | 8.8 | 9   | 3.6 | 92 | 176 |
| C18 | 7.4 | 4.88 | 18.6 | 45   | 92.2 | 38.1 | 41.3 | 145 | 30.8 | 2.3 | 10.6 | 9.1 | 0.1  | 6.8 | 8.5 | 8.8 | 5.2 | 90 | 168 |
| C20 | 7   | 5.25 | 19.2 | 47   | 89.4 | 36.5 | 40.8 | 241 | 26.9 | 1.9 | 11   | 9   | 0.16 | 6.6 | 8.4 | 8.7 | 4.6 | 88 | 168 |

TABLE 5-continued

| Reference Patients | WBC | RBC | HB | HCT | MCV | MCH | MCHC | PLT | LYM | LYC | RDW | RDS | PCT | MPV | PDW | PDS | MP | MR | MW |
|---|---|---|---|---|---|---|---|---|---|---|---|---|---|---|---|---|---|---|---|
| C15 | 4.8 | 4.86 | 18.3 | 45.6 | 93.8 | 37.8 | 40.2 | 144 | 28.3 | 1.4 | 12.3 | 9.6 | 0.1 | 7.1 | 9.7 | 9.6 | 3.6 | 88 | 164 |
| C17 | 6.7 | 5.44 | 19.6 | 47.8 | 87.9 | 36.1 | 41.1 | 193 | 37.4 | 2.5 | 11.3 | 9.3 | 0.13 | 6.8 | 8.6 | 8.9 | 4.6 | 86 | 174 |
| C21 | 6.9 | 4.82 | 18.2 | 44.6 | 92.5 | 37.8 | 40.9 | 138 | 23 | 1.6 | 11.1 | 9.3 | 0.09 | 6.6 | 8.6 | 8.9 | 4.6 | 90 | 192 |
| C22 | 7.1 | 5.08 | 18 | 44.7 | 88 | 35.5 | 40.3 | 191 | 38.7 | 2.8 | 11.4 | 9.2 | 0.13 | 6.7 | 8.4 | 8.6 | 5 | 86 | 176 |

TABLE 6

| | Sick | Healthy |
|---|---|---|
| Reference Patients | | |
| Amlgm1 | 1 | 0 |
| Amlgm2 | 1 | 0 |
| Amlgm3 | 1 | 0 |
| Amlgm4 | 1 | 0 |
| Amlgm6 | 1 | 0 |
| Amlgm7 | 1 | 0 |
| Amlgm8 | 1 | 0 |
| Amlgm9 | 1 | 0 |
| Amlgm10 | 1 | 0 |
| Amlgm11 | 1 | 0 |
| Amlgm13 | 1 | 0 |
| Amlgm14 | 1 | 0 |
| Amlgm15 | 1 | 0 |
| Amlgm16 | 1 | 0 |
| Amlgm17 | 1 | 0 |
| Amlgm20 | 1 | 0 |
| Amlgm23 | 1 | 0 |
| Amlgm24 | 1 | 0 |
| Amlgm25 | 1 | 0 |
| Healthy Patients | | |
| aC1 | 0 | 1 |
| aC2 | 0 | 1 |
| aC3 | 0 | 1 |
| aC4 | 0 | 1 |
| aC5 | 0 | 1 |
| aC7 | 0 | 1 |
| aC8 | 0 | 1 |
| C13 | 0 | 1 |
| C14 | 0 | 1 |
| C16 | 0 | 1 |
| C18 | 0 | 1 |
| C20 | 0 | 1 |
| C15 | 0 | 1 |
| C17 | 0 | 1 |
| C21 | 0 | 1 |
| C22 | 0 | 1 |

The second step involves the above described artificial neural network analytic model to select the matching disorder for the unknown and undiagnosed patient, and the associated PLS-Discriminant Analysis model, according to the above described process.

In the third and final step, predictions using the selected PLS-Discriminant Analysis model in step 2 are done in order to produce the diagnosis and the associated probability level. These are obtained by using one of the models (the selected model) developed in step 1. Again, the computation is carried out using Matlab® for Windows™ through use of the program called "PLSPRED.M".[6] In this case, input is made to the equation— ypred=plspred(x,b,P,Q,W,lv)

wherein
ypred is the predicted value, i.e., the diagnosis;
x is the matrix of input vectors, comprised of data from undiagnosed patients;

b is the vector of regression coefficients between x and y, calculated in the first step;
P is the matrix of x-loadings, calculated in the first step;
Q is the matrix of y-loadings, calculated in the first step;
W is the matrix of weights, calculated in the first step;
lv is the total number of latent variables, calculated in the first step function ypred=plspred(x,b,P,Q,W,lv)

```
% This program uses pls model parameters to predict the
% responses to an new x block. Input/output sequence is:
% ypred = plspred(x,b,P,Q,W,lv);
% Copyright
% Barry M. Wise
% 1991
[mx,nx] = size(x);
[mq,nq] = size(Q);
that = zeros(mx,lv);
ypred = zeros(mx,mq);
for i = 1:lv
    that(:,i) = x*W(:,i);
    x = x - that(:,i)*P(:,i)';
end
for i = 1:lv
    ypred = ypred + b(1,i)*that(:,i)*Q(:,i)';
end
```

After predictions have been obtained for the reference group in order to calculate E, the expected value in the equation below and the estimate of s, the standard deviation for the said reference group and for X, the predicted diagnosis, the t-value can be calculated as follows;

$$t=[X-E]/(s\sqrt{n})$$

wherein
X is the value predicted by the PLS discriminant analysis model;
E is the expected value for the appropriate reference group;
s is the standard deviation associated with the reference group;
n is the number of observations.

The t-value obtained in this manner can be compared to tabulated values in a standard t-distribution and the associated probability interval determined.

[6] The computer screen indicates that the program is the copyright of Barry M. Wise, 1991.

As noted above, the invention is applicable to the analyses from essentially any method employed to determine physical medical disorders. These methods are well established and the literature abounds with descriptions of how they are conducted. It would be well within the skill of the art to employ the data from such analysis in the method of the invention. A commonly employed method of determining physical medical disorder is by immunoassay. In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent, bioluminescence, fluorolumi-nescence, and the like, or radio label conjugate which comprises the chemiluminescent, bioluminescent, fluoroluminescent, and the like, or the radio label moiety, attached to a specific binding material. Specific binding material is any material which will bind specifically by an immunoreaction, protein binding reaction, nucleic acid hybridization reaction, and any other reaction in which the material reacts specifically with a restricted class of biological, biochemical or chemical species. In this category of assays, the conjugate participates in a specific binding reaction and the presence of analyte in the sample is proportional to the formation of one or more specific binding reaction products containing the conjugate. The assay is performed by allowing the requisite specific binding reactions to occur under suitable reaction conditions. The formation of specific binding reaction products containing the conjugate is determined by measuring the chemiluminescence, bioluminescence or fluoroluminescence or energy emissions of such products containing the conjugate or by measuring the luminescent or radio emitting properties of unreacted or partially reacted conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent, bioluminescent or fluorolumi-nescent moiety or radio label is attached, is capable of specifically binding with the analyte. The assay further utilizes a reactant which is capable of specifically binding with the analyte to form a reactant-analyte-labeled conjugate complex. The reactant may be attached to a solid phase, including without limitation, dip sticks, beads, tubes, paper or polymer sheets. In such cases, the presence of analyte in a sample will be proportional to the signal from the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the labeled moiety is attached, to form a labeled conjugate-reactant complex. The reactant may be attached to a solid phase, or alternatively reaction products containing the reactant may be precipitated by use of a second antibody or by other known means. In this competitive format the presence of analyte is "proportional," i.e., inversely proportional, to the signal from the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-labeled conjugate complex formed as a reaction product. This is illustrated by attaching the label to an antibody which is specific to a surface antigen on a cell. The presence of the cell surface antigen will be indicated by the signal from the cells after the completion of the reaction. The cells themselves may be used in conjunction with a filtration system to separate the analyte-label conjugate complex which is formed on the surface of the cell from unreacted labeled conjugate. This is discussed further in U.S. Pat. No. 4,652,533.

Other assay formats include sequential saturation and competitive displacement, both of which utilize a labeled conjugate, where in both involve (1) the specific binding material, to which the moiety is attached, and (2) the analyte specifically bind with a reactant. In the case of sequential saturation, the analyte is reacted with the reactant first, followed by a reaction of the conjugate with remaining unreacted reactant. In the case of competitive displacement, the conjugate competitively displaces analyte which has already bound to the reactant.

In a quenching format, the assay utilizes a reactant which is capable of specifically binding with the analyte to form an analyte-reactant complex and with the specific binding material, to which the signal label is attached, to form a conjugate-reactant complex. A quenching moiety is attached to the reactant. When brought into close proximity to the label, the quenching moiety reduces or quenches the signal from the label. In this quenching format the presence of analyte is proportional to the signal from the label. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the label conjugate may be reacted with the complex on the solid phase. Alternatively, the solid phase, sample and label conjugate may be added together simultaneously and reacted prior to separation. As a still further but less preferred alternative, the analyte in the sample and the luminescent conjugate may be reacted prior to addition of the reactant on the solid phase. Similar variations in the mixing and reaction steps are possible for competitive assay formats as well as other formats known in the art.

In the second category of assay formats, the assay utilizes an unconjugated label compound. The presence of analyte in the sample is proportional to the formation of one or more specific binding reaction products which do not themselves contain the label. Instead, the label's signal is in proportion to the formation of such reaction products. In one example of this second category of assays, the assay utilizes a reactant capable of binding with the analyte to form an analyte-reactant complex which causes the signal from the label. This is illustrated by a simple enzyme-substrate assay in which the analyte is the substrate glucose and the reactant is the enzyme glucose oxidase. Formation of the enzyme-substrate complex triggers the luminescent compound. Such enzyme-substrate assay for glucose is disclosed in U.S. Pat. Nos. 3,964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the luminescent compound to luminesce.

Also included in the second category of assays are those assays in which the formation of the reaction products promotes or inhibits the signal by the label in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the label. Analyte in the sample, however, will tie up the second reactant, thus preventing the second reactant from inhibiting the production of peroxide. The presence of analyte will be proportional to the signal from the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-label conjugate complex is separated from unreacted label conjugate. In a surface antigen assay, the analyte-label conjugate complex is separated form unreacted label conjugate. In a competitive assay, the reactant-label conjugate complex is separated from unreacted label conjugate. In a sequential saturation assay and in a competitive displacement assay, the reactant-label conjugate complex is separated from unreacted label conjugate. Alternatively, in homogeneous assays the reaction products are not separated. After the assay reagents have been allowed to react, the signal may be measured from the whole assay mixture whether such mixture is in solution, on a solid phase or distributed between various membrane layers of a dip stick or other solid support. The glucose assay using glucose oxidase and a label moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Other immunological antigen-antibody reactions methods suitable for generating the data for use in the method of the invention include, without limitation, turbidometry/nefelometry, electroimmunoassay (EIA), fluorescence polarized immunoassay (FPIA), electrophoresis, enzyme immunoassay (EIA), microparticle enzyme immunoassay (MEIA), and the like.

Wet and dry chemical analyses are an abundant source of data for the method of the invention. Analyses by large autoanalyzers can be used to generate such data. Chemical reactions that yield colored complexes, measured by spectrophotometry, for electrolytes, alkaline earth metal ions, and the like. Such can be effected also by the ion selective electrodes (ISE) method.

Measurements of enzymes such as alanine amino transferase, aspartate amino transferase, and the like; creatinin, urea, glucose, lactate, and drugs such as salicylate, paracetamol, and the like, are suitable data for the process of the invention.

Chromatographic analysis by HPLC, GC, GC/MS and liquid chromatography-mass spectrometry (LC/MS) can be used for data relative to serotonin metabolites, hemoglobin, catechol amines, adrenaline, noradrenaline, dopamine, alcohols such as methanol, ethanol, n-propanol, and the like.

The data can be that generated by an amino acid sequenator relating to amino acid sequencing and DNA analysis, or by polymerase chain reaction (PCR) as used in forensic sciences, and coagulation techniques such as clotting analysis and chromogen substrate analysis.

We claim:

1. A process for analyzing for a variety of physical medical disorders, which comprises:

a) clinical testing by common analyses, samples of patients free of certain physical medical disorders encompassed by said variety of physical medical disorders and samples of patients that possess one or more of such variety of disorders, to obtain clinical testing of such variety of disorders as derived from such samples, which analyses distinguish such disorders thereby obtaining the characterization of a collection of such disorders as numerical data;

b) scaling the matrix of said numerical data in a computer;

c) configuring in a computer, an artificial neural network prescribed by the number of variables and the number of disorders, which artificial neural network is electronic data that possesses an input layer, one or more hidden layers and an output layer;

d) fitting the artificial neural network electronic data in a computer to the numerical data according to adjustable parameters of the artificial neural network;

e) whereby the artificial neural network is trained in the computer to automatically provide a analytic model;

f) withdrawing from a new patient that has not been diagnosed for such disorder, a sample or samples of a kind taken from said reference patients and subjecting said diagnostic sample to said clinical testing to obtain new numerical data;

g) automatically scaling in the computer the new data to the data derived from the reference patients;

h) feeding the scaled new data to the trained artificial neural network and the analytic model thereof, and i) automatically obtaining a diagnosis of the new patient with respect to such disorders.

2. The process of claim 1 wherein the clinical testing involves diagnostic procedures that involve determining the nature and cause of 1 disease or injury through evaluation of patient history, examination, and review of laboratory data.

3. The process of claim 2 wherein the laboratory data includes the diagnostic analysis of bodily fluids, cells, soft and hard tissues, and organs.

4. The process of claim 3 wherein the data is from one or more of immunoassays, wet and dry chemical analysis, hematological analysis, cell size analysis, chromatographic analysis, spectrographic analysis, electrochemical analysis, pH analysis, ion selective potentiometry, NIR, ISS, SIMS, AES, ICP-MS, AAS, LC/MS, nuclear magnetic resonance spectrometry, nuclear magnetic imaging techniques, chemical elemental analysis, and gas analysis including gas chromatography, antibody analysis, blotting techniques, electrophoresis, amino acid sequencing, and DNA analysis.

5. The process of claim 1 wherein the obtained numerical data characterizes deviations from the data of healthy patients as well as data that correlates with the data of the reference group patients that possess the disorder.

6. The process of claim 1 wherein the obtained diagnosis provides the best matching reference group and thereby assigning the particular disorder for the physician.

7. The process of claim 1 wherein if no matching disorder is provided by the obtained diagnosis, any abnormality of the sample is flagged.

8. The process of claim 1 wherein autoscaling is done by analog or digital means and the translations are computed by computer.

9. The process of claim 8 wherein translating the data is effected on a computer through digital conversions.

10. The process of claim 1 wherein the artificial neural network is optimized by (i) determining the right number of hidden layers, (ii) the right number of neurons in the hidden layers, and (iii) overall training of the network.

11. The process of claim 10 wherein (i) and (ii) are chosen by configuring the network by a pre-chosen number and training the network, calculating prediction error between real and model values, storing this data and choosing the next higher number for number (i) and (ii) above.

12. The process of claim 11 wherein the pre-chosen number is at least one hidden layer and at least two neurons.

13. The process of claim 12 wherein the new network is trained, prediction error is calculated and stored, and this process is repeated until a minimum prediction error is attained.

* * * * *